US009840494B2

(12) United States Patent
Zhang et al.

(10) Patent No.: US 9,840,494 B2
(45) Date of Patent: Dec. 12, 2017

(54) QUINAZOLINE DERIVATIVE

(71) Applicant: Tianjin Hemay Oncology Pharmaceutical Co., Ltd., Tianjin (CN)

(72) Inventors: Hesheng Zhang, Tianjin (CN); Guanghuai Zeng, Tianjin (CN); Yingwei Chen, Tianjin (CN)

(73) Assignee: Tianjin Hemay Oncology Pharmaceutical Co., Ltd., Tianjin (CN)

( * ) Notice: Subject to any disclaimer, the term of this patent is extended or adjusted under 35 U.S.C. 154(b) by 0 days.

(21) Appl. No.: 15/103,596

(22) PCT Filed: Dec. 12, 2014

(86) PCT No.: PCT/CN2014/001119
§ 371 (c)(1),
(2) Date: Jun. 10, 2016

(87) PCT Pub. No.: WO2015/085654
PCT Pub. Date: Jun. 18, 2015

(65) Prior Publication Data
US 2016/0311796 A1 Oct. 27, 2016

(30) Foreign Application Priority Data
Dec. 12, 2013 (CN) .......................... 2013 1 0706058

(51) Int. Cl.
*C07D 401/12* (2006.01)
(52) U.S. Cl.
CPC ................................. *C07D 401/12* (2013.01)
(58) Field of Classification Search
CPC .................................................. C07D 401/12
See application file for complete search history.

(56) References Cited

U.S. PATENT DOCUMENTS

| 7,754,729 | B2 * | 7/2010 | Zhang | C07D 239/94 514/266.4 |
|---|---|---|---|---|
| 8,198,301 | B2 * | 6/2012 | Zhang | C07D 215/54 514/313 |
| 8,765,946 | B2 * | 7/2014 | Zhang | C07D 215/54 544/293 |
| 9,187,458 | B2 * | 11/2015 | Zhang | C07D 401/12 |
| 2002/0077330 | A1 | 6/2002 | Himmelsbach et al. | |
| 2009/0105247 | A1 * | 4/2009 | Zhang | C07D 239/94 514/234.5 |
| 2010/0240649 | A1 * | 9/2010 | Zhang | C07D 215/54 514/234.5 |
| 2012/0225872 | A1 * | 9/2012 | Zhang | C07D 215/54 514/234.5 |
| 2013/0225579 | A1 * | 8/2013 | Zhang | C07D 401/12 514/235.2 |
| 2016/0185728 | A1 * | 6/2016 | Zhang | C07D 401/12 514/235.2 |

FOREIGN PATENT DOCUMENTS

| CN | 101100466 A | 1/2008 |
|---|---|---|
| EP | 2045245 A1 | 4/2009 |
| JP | 2009518450 A | 5/2009 |
| JP | 2010502744 A | 1/2010 |
| JP | 2013504521 A | 2/2013 |
| WO | 2012104206 A1 | 8/2012 |
| WO | 2013013640 A1 | 1/2013 |

OTHER PUBLICATIONS

J. Luo et al., 36 Cell, 823-837 (2009).*
National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
Z. Wang et al., 19 Drug Discovery Today, 145-150 (2014).*
U.K. Marelli et al., 3 Frontiers in Oncology, 1-12 (2013).*
R.D. Prasasya et al., 21 Seminars in Cancer Biology, 200-206 (2011).*
Kinase Inhibitors, Methods in Molecular Biology 795 (B. Kuster ed., 2012).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).*
R-D Li et al., 21 Bioorganic & Medicinal Chemistry Letters, 3637-3640 (2011).*
M.N. Noolvi et al., 46 European Journal of Medicinal Chemistry, 2327-2346 (2011).*
R. Stupp et al., 25 Journal of Clinical Oncology, 1637-1638 (2007).*
A.M. Jubb et al., 6, Nature Reviews | Cancer 626-635 (2006).*
McDermott et al., 27 Journal of Clinical Oncology, 5650-5659 (2009).*
C.L. Sawyers, Nature, 548-552 (2008).*
C.M. Coughlin et al., Breast Cancer Research Treatment, 1-11 (2010).*
I Mirkina et al., 9 PlOS ONE, 1-13 (2014).*
Translation of the International Search Report and Written Opinion corresponding to International Patent Application No. PCT/CN2014/001119, dated Mar. 18, 2015, 8 pages.
Japanese Patent Application No. 2016-539159, Office Action dated Aug. 8, 2017, with English translation, 8 pages.
Berge, S.M. et al., Pharmaceutical Salts, Journal of Pharmaceutical Sciences, Jan. 1977, 66(1), pp. 1-19.
Anderson, B.D., et al., Practice of Medicinal Chemistry, 1999, pp. 347-365, ed. C.G. Wermuth.
Gould, P.L., Salt selection for basic drugs, Int'l. J. of Pharmaceutics, vol. 33, Nov. 1986, pp. 201-217.
Bastin, R.J., et al., Salt Selection and Optimisation Procedures for Pharmaceutical New Chemical Entities, Org. Proc. Res. Dev., 2000, 4 (5), pp. 427-435.

* cited by examiner

*Primary Examiner* — Alexander R Pagano
(74) *Attorney, Agent, or Firm* — Lathrop Gage LLP

(57) ABSTRACT

Disclosed are N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof.

13 Claims, No Drawings

QUINAZOLINE DERIVATIVE

RELATED APPLICATION

The present application is a 35 U.S.C. §371 filing of International Application No. PCT/CN2014/001119, filed Dec. 12, 2014, which claims priority to and relevant benefits of the Chinese patent application No. 201310706058.3, entitled "Quinazoline Derivative with Antitumor Activity, Preparation and Application thereof" and filed with the State Intellectual Property Office of China on Dec. 12, 2013. Each of the aforementioned applications is hereby incorporated by reference in its entirety.

FIELD

The present application relates to the field of pharmaceutical chemistry.

BACKGROUND

EGFR is a member of the HER (human epidermal growth factor receptor) glycoprotein family, other members of the family include ErbB2 (HER-2), ErbB3 (HER-3), ErbB4 (HER-4). The intracellular EGFR tyrosine kinase can catalyze the phosphorylation of various substrate proteins, and plays a pivotal role in the signaling pathway of tumor cells. EGFR can activate its intracellular tyrosine kinase under the stimulus of an extracellular signal, transmit the extracellular signal into cells and amplify the signal, thereby regulating the growth and differentiation of cells, angiogenesis and inhibition of apoptosis. Abnormal signaling pathway transmission caused by EGFR over-expression or mutation has a close correlation with the growth, invasion and metastasis of malignant tumors. EGFR expression is progressively increased from normal tissues, pre-cancerous lesions to cancerous tissue, and the EGFR expression level is closely related to the prognosis of cancer patients. Several synthetic drugs can block EGFR-mediated signal transduction, thereby inhibiting the growth of tumor cells and the tumor invasion into surrounding tissue, and promoting the apoptosis of tumor cells. Therefore, EGFR-targeted therapy is one of the current research hot spots. Molecular targeted therapy targeting EGFR has good therapeutic effect in selective population.

Currently, drugs targeting EGFR on the market are mainly divided into two categories: monoclonal antibodies which act on the extracellular domain of EGFR, and small-molecule EGFR tyrosine kinase inhibitors (EGFR-TKI) which act on the binding domain of the intracellular EGFR tyrosine kinase. Moreover, EGFR-TKI drugs are classified into two categories (i.e. reversible and irreversible inhibitors) due to the different binding modes between the drugs and the EGFR tyrosine kinase. Irreversible inhibitors can irreversibly and permanently bind to the protein tyrosine kinase, and continuously reduce the level of the protein tyrosine kinase unless new protein tyrosine kinase is generated. Irreversible inhibitors have longer medicinally effective time. However, FDA application records show that the bioavailability of the existing clinically developed drug Afatinib is merely 11.175%; in the xenograft model using A431 human epidermal carcinoma nude mice, 10 mg/kg dosage of Afatinib shows no pharmacological effect. However, the MTD of Afatinib is 30 mg/kg (see Li D, Ambrogio L, Shimamura T, et al. BIBW2992, an irreversible EGFR/HER2 inhibitor highly effective in preclinical lung cancer models. Oncogene, 2008, 27(34): 4702-4711). Therefore, it is apparent that the therapeutic window of Afatinib is very narrow.

SUMMARY

One aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof.

Another aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof, wherein the acid which is used to form the salt is selected from the group consisting of hydrochloric acid, hydrobromic acid, sulfuric acid, nitric acid, phosphoric acid, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid and undecylenic acid.

Still another aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof, wherein the salt is selected from the group consisting of:
N-[4-(3-chloro-4-fluorophenylamino)-7-(2-methoxyethoxy)quinazolin-6-yl]-2-[1-(2-methoxyethyl)piperidin-4-ylidene]acetamide dihydrochloride;
N-[4-(3-chloro-4-fluorophenylamino)-7-(2-methoxyethoxy)quinazolin-6-yl]-2-[1-(2-methoxyethyl)piperidin-4-ylidene]acetamide disulfate;
N-[4-(3-chloro-4-fluorophenylamino)-7-(2-methoxyethoxy)quinazolin-6-yl]-2-[1-(2-methoxyethyl)piperidin-4-ylidene]acetamide dihydrobromide;
N-[4-(3-chloro-4-fluorophenylamino)-7-(2-methoxyethoxy)quinazolin-6-yl]-2-[1-(2-methoxyethyl)piperidin-4-ylidene]acetamide dinitrate;
N-[4-(3-chloro-4-fluorophenylamino)-7-(2-methoxyethoxy)quinazolin-6-yl]-2-[1-(2-methoxyethyl)piperidin-4-ylidene]acetamide diphosphate;
N-[4-(3-chloro-4-fluorophenylamino)-7-(2-methoxyethoxy)quinazolin-6-yl]-2-[1-(2-methoxyethyl)piperidin-4-ylidene]acetamide diacetate;
N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate;
N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate;

N-[4-(3-chloro-4-fluorophenylamino)-7-(2-methoxyethoxy)
    quinazolin-6-yl]-2-[1-(2-methoxyethyl)piperidin-4-
    ylidene]acetamide difumarate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dimaleate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dinicotinate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dioleate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dioxalate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dipropionate;
N-[4-(3-chloro-4-fluorophenylamino)-7-(2-methoxyethoxy)
    quinazolin-6-yl]-2-[1-(2-methoxyethyl)piperidin-4-
    ylidene]acetamide disalicylate;
N-[4-(3-chloro-4-fluorophenylamino)-7-(2-methoxyethoxy)
    quinazolin-6-yl]-2-[1-(2-methoxyethyl)piperidin-4-
    ylidene]acetamide bis(4-aminosalicylate);
N-[4-(3-chloro-4-fluorophenylamino)-7-(2-methoxyethoxy)
    quinazolin-6-yl]-2-[1-(2-methoxyethyl)piperidin-4-
    ylidene]acetamide diacetylsalicylate;
N-[4-(3-chloro-4-fluorophenylamino)-7-(2-methoxyethoxy)
    quinazolin-6-yl]-2-[1-(2-methoxyethyl)piperidin-4-
    ylidene]acetamide ditartrate;
N-[4-(3-chloro-4-fluorophenylamino)-7-(2-methoxyethoxy)
    quinazolin-6-yl]-2-[1-(2-methoxyethyl)piperidin-4-
    ylidene]acetamide di(p-toluenesulfonate);
N-[4-(3-chloro-4-fluorophenylamino)-7-(2-methoxyethoxy)
    quinazolin-6-yl]-2-[1-(2-methoxyethyl)piperidin-4-
    ylidene]acetamide dicitrate;
N-[4-(3-chloro-4-fluorophenylamino)-7-(2-methoxyethoxy)
    quinazolin-6-yl]-2-[1-(2-methoxyethyl)piperidin-4-
    ylidene]acetamide dimalate;
N-[4-(3-chloro-4-fluorophenylamino)-7-(2-methoxyethoxy)
    quinazolin-6-yl]-2-[1-(2-methoxyethyl)piperidin-4-
    ylidene]acetamide bis(naphthalene-1,5-disulfonate);
N-[4-(3-chloro-4-fluorophenylamino)-7-(2-methoxyethoxy)
    quinazolin-6-yl]-2-[1-(2-methoxyethyl)piperidin-4-
    ylidene]acetamide bis(decanedioate); and
N-[4-(3-chloro-4-fluorophenylamino)-7-(2-methoxyethoxy)
    quinazolin-6-yl]-2-[1-(2-methoxyethyl)piperidin-4-
    ylidene]acetamide bis(L-aspartate).

Yet another aspect of the present application relates to a pharmaceutical composition comprising N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof, and a pharmaceutically acceptable carrier, diluent or excipient.

Still another aspect of the present application relates to a process for preparing N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof, comprising:

reacting a compound represented by Formula (I) with a compound represented by Formula (II) to obtain the compound N-[4-(3-chloro-4-fluorophenylamino)-7-(2-methoxyethoxy)quinazolin-6-yl]-2-[1-(2-methoxyethyl)piperidin-4-ylidene]acetamide; preferably converting the compound represented by Formula (I) into an activated ester, acyl chloride, acylated imidazole or mixed anhydride, which is then reacted with the compound represented by Formula (II), more preferably adding a tertiary amine such as triethylamine, N-methylmorpholine, trimethylamine, pyridine or substituted pyridine as a catalyst, and in the case of converting the compound represented by Formula (I) into acyl chloride, preferably using thionyl chloride, phosphorus trichloride, phosphorus pentachloride, phosphorus oxychloride, oxalyl chloride, or cyanuric chloride as a chlorinating agent; or preferably converting the compound represented by Formula (I) into an anhydride, which is then reacted with the compound represented by Formula (II), more preferably adding pyridine, substituted pyridine such as DMAP as a catalyst;

optionally, reacting the compound N-[4-(3-chloro-4-fluorophenylamino)-7-(2-methoxyethoxy)quinazolin-6-yl]-2-[1-(2-methoxyethyl)piperidin-4-ylidene]acetamide with a pharmaceutically acceptable acid to give its corresponding pharmaceutically acceptable salt;

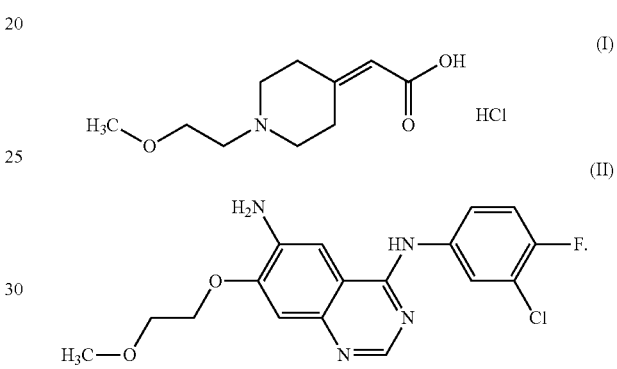

Another aspect of the present application relates to a method for the treatment or prevention of a disease associated with protein kinase, comprising administering to a subject in need thereof a therapeutically or prophylactically effective amount of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof.

Still another aspect of the present application relates to a method for the treatment or prevention of physiological abnormality caused by over-expression of protein tyrosine phosphorylation enzyme in mammal, comprising administering to a mammal in need thereof a therapeutically or prophylactically effective amount of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof.

A further aspect of the present application relates to use of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof in the manufacture of a medicament for the treatment or prevention of a disease associated with protein kinase, preferably in the manufacture of a medicament for the treatment or prevention of physiological abnormality caused by over-expression of protein tyrosine phosphorylation enzyme in mammal.

Yet another aspect of the present application relates to use of a pharmaceutical composition comprising N-[4(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof in the manufacture of a medicament for the treatment or prevention of a disease associated with protein kinase, preferably in the manufacture of a medicament for the treatment or prevention of physiological abnormality caused by over-expression of protein tyrosine phosphorylation enzyme in mammal.

DETAIL DESCRIPTION

In the following description, certain specific details are included to provide a thorough understanding for variously disclosed embodiments. One skilled in the relevant art, however, will recognize that the embodiments may be practiced without one or more these specific details, or with other methods, components, materials, etc.

Unless the context specifies otherwise, throughout the specification and claims which follow, the terms "comprise, comprising, comprises" and "include, including, includes" are to be construed in open, inclusive senses, which shall be construed as "include, but are not limited to".

Reference throughout this specification to "one embodiment", or "an embodiment", or "in another embodiment", or "in some embodiments" means that a particular referenced feature, structure or characteristic described in connection with the embodiment(s) is included in at least one embodiment. Therefore, the phrases "in one embodiment", or "in the embodiment", or "in another embodiment", or "in some embodiments" appeared in various places throughout this specification are not necessarily all referring to the same embodiment. Moreover, the particular features, structures or characteristics may be combined in any suitable manner in one or more embodiments.

Definitions

"Pharmaceutically acceptable carrier, diluent or excipient" includes, without limitation, any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and has no side effect on the preparation of a pharmaceutical composition.

"Pharmaceutically acceptable salt" refers to those salts which retain the biological efficacy and properties of the free bases, which are not biologically or otherwise undesirable, and which are formed with inorganic acids such as, but not limited to hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid, undecylenic acid and the like.

"Pharmaceutical composition" refers to a formulation formed from a compound of the present application and a medium generally acceptable in the art for the delivery of the biologically active compound to mammals, e.g., humans Such a medium includes all pharmaceutically acceptable carriers, diluents or excipients.

"Therapeutically effective amount" refers to an amount of a compound of the present application which, when administered to mammal such as human, is sufficient to show effects, as defined below, to a disease or condition that is mediated by a protein tyrosine phosphorylation enzyme in the mammal such as human. The amount of a compound of the present application which constitutes a "therapeutically effective amount" will vary depending on the compound, the disease or condition and its severity, and the age of the mammal to be treated, but can be determined routinely by one of ordinary skill in the art having regard to his own knowledge and to this disclosure.

"Treating" or "treatment" as used herein covers the treatment of the disease or condition of interest in mammal such as human, having the disease or disorder of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development; or (iii) relieving the disease or condition, i.e., causing regression of the disease or condition.

As used herein, the terms "disease" and "condition" may be used interchangeably or may be different in that particular malady or condition may not have a known causative agent (so that etiology has not yet been worked out) and it is therefore not yet recognized as a disease but only as an undesirable condition or syndrome, wherein a more or less specific set of symptoms have been identified by clinicians.

Specific Embodiments

One aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof.

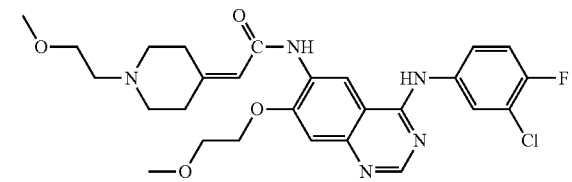 [SMILES: COCCOc1cc2ncnc(Nc3ccc(F)c(Cl)c3)c2cc1NC(=O)C=C1CCN(CCOC)CC1]

N-[4-(3-chloro-4-fluorophenylamino)-7-(2-methoxyethoxy)quinazolin-6-yl]-2-[1-(2-methoxyethyl)piperidin-4-ylidene]acetamide Another aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof, wherein the acid which is used to form the salt is selected from the group consisting of hydrochloric acid, hydrobromic acid, sulfuric acid, nitric acid, phosphoric acid, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid and undecylenic acid.

Still another aspect of the present application relates to N-[4-(3-chloro-4-fluorophenylamino)-7-(2-methoxyethoxy)quinazolin-6-yl]-2-[1-(2-methoxyethyl)piperidin-4-ylidene]acetamide and a pharmaceutically acceptable salt thereof, wherein the salt is selected from the group consisting of:

N-[4-(3-chloro-4-fluorophenylamino)-7-(2-methoxyethoxy)quinazolin-6-yl]-2-[1-(2-methoxyethyl)piperidin-4-ylidene]acetamide dihydrochloride;
N-[4-(3-chloro-4-fluorophenylamino)-7-(2-methoxyethoxy)quinazolin-6-yl]-2-[1-(2-methoxyethyl)piperidin-4-ylidene]acetamide disulfate;
N-[4-(3-chloro-4-fluorophenylamino)-7-(2-methoxyethoxy)quinazolin-6-yl]-2-[1-(2-methoxyethyl)piperidin-4-ylidene]acetamide dihydrobromide;
N-[4-(3-chloro-4-fluorophenylamino)-7-(2-methoxyethoxy)quinazolin-6-yl]-2-[1-(2-methoxyethyl)piperidin-4-ylidene]acetamide dinitrate;
N-[4-(3-chloro-4-fluorophenylamino)-7-(2-methoxyethoxy)quinazolin-6-yl]-2-[1-(2-methoxyethyl)piperidin-4-ylidene]acetamide diphosphate;
N-[4-(3-chloro-4-fluorophenylamino)-7-(2-methoxyethoxy)quinazolin-6-yl]-2-[1-(2-methoxyethyl)piperidin-4-ylidene]acetamide diacetate;
N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate;
N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate;
N-[4-(3-chloro-4-fluorophenylamino)-7-(2-methoxyethoxy)quinazolin-6-yl]-2-[1-(2-methoxyethyl)piperidin-4-ylidene]acetamide difumarate;
N-[4-(3-chloro-4-fluorophenylamino)-7-(2-methoxyethoxy)quinazolin-6-yl]-2-[1-(2-methoxyethyl)piperidin-4-ylidene]acetamide dimaleate;
N-[4-(3-chloro-4-fluorophenylamino)-7-(2-methoxyethoxy)quinazolin-6-yl]-2-[1-(2-methoxyethyl)piperidin-4-ylidene]acetamide dinicotinate;
N-[4-(3-chloro-4-fluorophenylamino)-7-(2-methoxyethoxy)quinazolin-6-yl]-2-[1-(2-methoxyethyl)piperidin-4-ylidene]acetamide dioleate;
N-[4-(3-chloro-4-fluorophenylamino)-7-(2-methoxyethoxy)quinazolin-6-yl]-2-[1-(2-methoxyethyl)piperidin-4-ylidene]acetamide dioxalate;
N-[4-(3-chloro-4-fluorophenylamino)-7-(2-methoxyethoxy)quinazolin-6-yl]-2-[1-(2-methoxyethyl)piperidin-4-ylidene]acetamide dipropionate;
N-[4-(3-chloro-4-fluorophenylamino)-7-(2-methoxyethoxy)quinazolin-6-yl]-2-[1-(2-methoxyethyl)piperidin-4-ylidene]acetamide disalicylate;
N-[4-(3-chloro-4-fluorophenylamino)-7-(2-methoxyethoxy)quinazolin-6-yl]-2-[1-(2-methoxyethyl)piperidin-4-ylidene]acetamide bis(4-amino salicylate);
N-[4-(3-chloro-4-fluorophenylamino)-7-(2-methoxyethoxy)quinazolin-6-yl]-2-[1-(2-methoxyethyl)piperidin-4-ylidene]acetamide diacetylsalicylate;
N-[4-(3-chloro-4-fluorophenylamino)-7-(2-methoxyethoxy)quinazolin-6-yl]-2-[1-(2-methoxyethyl)piperidin-4-ylidene]acetamide ditartrate;
N-[4-(3-chloro-4-fluorophenylamino)-7-(2-methoxyethoxy)quinazolin-6-yl]-2-[1-(2-methoxyethyl)piperidin-4-ylidene]acetamide di(p-toluenesulfonate);
N-[4-(3-chloro-4-fluorophenylamino)-7-(2-methoxyethoxy)quinazolin-6-yl]-2-[1-(2-methoxyethyl)piperidin-4-ylidene]acetamide dicitrate;
N-[4-(3-chloro-4-fluorophenylamino)-7-(2-methoxyethoxy)quinazolin-6-yl]-2-[1-(2-methoxyethyl)piperidin-4-ylidene]acetamide dimalate;
N-[4-(3-chloro-4-fluorophenylamino)-7-(2-methoxyethoxy)quinazolin-6-yl]-2-[1-(2-methoxyethyl)piperidin-4-ylidene]acetamide bis(naphthalene-1,5-disulfonate);
N-[4-(3-chloro-4-fluorophenylamino)-7-(2-methoxyethoxy)quinazolin-6-yl]-2-[1-(2-methoxyethyl)piperidin-4-ylidene]acetamide bis(decanedioate); and
N-[4-(3-chloro-4-fluorophenylamino)-7-(2-methoxyethoxy)quinazolin-6-yl]-2-[1-(2-methoxyethyl)piperidin-4-ylidene]acetamide bis(L-aspartate).

Yet another aspect of the present application relates to a pharmaceutical composition, comprising N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof, and a pharmaceutically acceptable carrier, diluent or excipient.

Examples of the pharmaceutically acceptable carrier that can be used in the pharmaceutical composition of the present application include, but are not limited to, any adjuvant, carrier, excipient, glidant, sweetening agent, diluent, preservative, dye/colorant, flavor enhancer, surfactant, wetting agent, dispersing agent, suspending agent, stabilizer, isosmotic agent, solvent, or emulsifier, etc, which has been approved by the United States Food and Drug Administration as being acceptable for use in humans or animals and has no side effects on the preparation of a pharmaceutical composition.

In some embodiments, a pharmaceutical composition of the present application can be formulated as tablet, solution, granule, patch, ointment, capsule, aerosol or suppository administered via parenteral, transdermal, mucosa, nasal, buccal, sublingual or oral route. The pharmaceutical composition of the present application can be administrated by oral administration, buccal administration, intravenous injection, intraperitoneal injection, subcutaneous injection, intramuscular injection, nasal drops, eye drops, inhalation, rectal administration, vaginal administration or epidermal administration.

Still another aspect of the present application relates to a process for preparing N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof, comprising:

reacting a compound represented by Formula (I) with a compound represented by Formula (II) to obtain the compound N-[4-((3-chloro-4-fluorophenylamino))-7-((2-methoxyethoxy))quinazolin-6-yl]-2-[1-((2-methoxyethyl))piperidin-4-ylidene]acetamide; preferably converting the compound represented by Formula (I) into an activated ester, acyl chloride, acylated imidazole or mixed anhydride, which is then reacted with the compound represented by Formula (II), more preferably adding a tertiary amine such as triethylamine, N-methylmorpholine, trimethylamine, pyridine or substituted pyridine as a catalyst, and in the case of converting the compound represented by Formula (I) into acyl chloride, preferably using thionyl chloride, phosphorus trichloride, phosphorus pentachloride, phosphorus oxychloride, oxalyl chloride, cyanuric chloride as a chlorinating agent; or preferably converting the compound represented by Formula (I) into an anhydride, which is then reacted with the compound represented by Formula (II), more preferably adding pyridine, substituted pyridine such as DMAP as the catalyst;

optionally, reacting the compound N-[4-(3-chloro-4-fluorophenylamino)-7-(2-methoxyethoxy)quinazolin-6-yl]-2-[1-(2-methoxyethyl)piperidin-4-ylidene]acetamide with a pharmaceutically acceptable acid thereof to give its corresponding pharmaceutically acceptable salt;

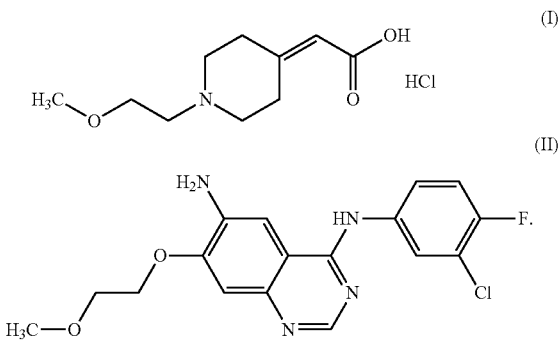

In some embodiments, the compound represented by Formula (II) is prepared according to the method described in U.S. patent publication No. US 2002/077330 A1.

In some embodiments, the compound represented by Formula (I) is prepared as follows:

1084.2 g (7.8 mol) of 2-bromoethylmethylether, 921.0 g (6 mol) of 4-piperidone monohydrate hydrochloride, 3312.0 g (24 mol) of anhydrous potassium carbonate and 3.75 L of N,N-dimethylacetamide were added into a reaction kettle (20 L), and stirred at room temperature for 24 hours. The volume of the reaction solution in the kettle was approximately 4.4 L. 2.2 L of the reaction solution was drained off, and 13 L of water and 4 L of dichloromethane were added into the kettle under stirring for 10 min, the resulting mixture was allowed to stand for liquid separation, and then the dichloromethane layer was drawn off. The aqueous layer is extracted with dichloromethane (3 L×3). The aqueous layer is discarded. The organic layers were combined, dried over anhydrous magnesium sulfate (1.3 kg) for half an hour, and then filtered under reduced pressure. The filter cake was washed with dichloromethane (1 L). The filter cake was filtered under reduced pressure to dryness, then discarded. Additional 2.2 L of reaction solution is treated as above. The filtrates were combined and concentrated by rotary evaporation. The concentrated solutions were combined to give an oily substance.

The oily substance was distilled under reduced pressure to collect the fraction at 82-88° C. under 2 mmHg, thereby obtaining 1-(2-methoxyethyl)piperidin-4-one (582.7g) as a colorless transparent liquid.

174.1g of sodium hydride (4.354 mol, content of 60%) and 5.08 L of dichloromethane were added into a reaction kettle (20 L). The mixture was stirred and cooled to 0° C. 660.4g (3.628 mol) of trimethyl phosphonoacetate was slowly added dropwise. While dropwise adding it, the temperature in the kettle was stably maintained ≤0° C. During the dropwise addition, large amount of gas was generated and the reaction solution was changed from gray to white. When the dropwise addition was completed, no more gas was released and the reaction solution was a white slurry. The reaction solution was maintained in a low temperature ≤0° C. with stirring for 1 hour. 577.7 g (3.628 mol) of 1-(2-methoxyethyl)piperidin-4-one was slowly added dropwise into the kettle. The temperature in the kettle was maintained ≤2° C. during the dropwise addition. After the dropwise addition was completed, the reaction solution was maintained in a low temperature of 0° C. under stirring for 15 hour.

After the reaction was completed, 1 L of water was added to terminate the reaction. The cooling was stopped. 4.08 L of water was added under stirring for 10 min, and then the reaction solution was allowed to stand for liquid separation. The dichloromethane layer was drawn off, and the aqueous layer was extracted with dichloromethane (1.7 L). The aqueous layer was discarded. The organic layers were combined and washed once with water (5.08 L) and extracted twice with 1N hydrochloric acid (3.6 L+1.5 L). The dichloromethane layer was then discarded and the hydrochloric acid layers were combined. The combined hydrochloric acid layer was cooled to about 0° C. 1N sodium hydroxide solution was slowly added dropwise thereto under stirring until pH reached 9. The cooling was stopped and the mixture was warmed up to room temperature. Then 5.08 L of dichloromethane was added for extraction. The aqueous layer was discarded, and the organic layer was washed once with water (5.08 L) and once with saturated sodium chloride solution (5.08 L). The organic layer was dried over anhydrous magnesium sulfate (500 g) for half an hour and filtered under reduced pressure. The filter cake was washed with 0.5 L of dichloromethane. The filtrate was dried under reduced pressure with an oil pump after rotary evaporation to dryness, to give a bright yellow oily substance.

621.0 g (2.915 mol) of methyl 2-[1-(2-methoxyethyl)-piperidin-4-ylidene]acetate and 2.915 L of ethanol were added into a reaction kettle (20 L), stirred and cooled to 0° C. 291.5 g (7.289 mol) of sodium hydroxide was dissolved in 0.729 L of water, and then cooled to 10° C. The resulting solution was maintained at low temperature and slowly added dropwise into the kettle. After the addition of sodium hydroxide was completed, the reaction solution was warmed up to 25° C., and the stirring was continued for 7 hours. After the reaction was completed, the reaction solution was cooled to 0° C. and stirred overnight.

To the reaction solution, concentrated hydrochloric acid was slowly added dropwise until pH reached 2, while the temperature was maintained at about 0° C. The cooling was stopped and the stirring was continued for 30 min at room temperature. The reaction solution was filtered in vacuo. The filter cake was washed with anhydrous ethanol (500 ml), and then filtered under reduced pressure to dryness and preserved. The filtrate was concentrated by rotary evaporation in a water bath at 50° C. until no liquid was evaporated, to give a yellow oily substance, and a large number of white crystals were precipitated. Then 1.46 L of anhydrous ethanol was added, stirred at room temperature for 15 min and filtered under reduced pressure. The filter cake was washed with anhydrous ethanol (500 ml) and then filtered under reduced pressure to dryness and preserved. The filtrate was concentrated by rotary evaporation at 50° C. until no liquid was evaporated, to give a pale yellow, thick porridge-like substance.

Recrystallization of the porridge-like substance: to the porridge-like substance was added to 1.46 L of isopropyl alcohol. The resulting mixture was stirred, refluxed and dissolved for clarification in a water bath at 85° C. A hot filtration under reduced pressure was carried out to remove a small amount of insoluble residues. The filtrate was transferred to a three-necked flask (3 L) and put into a water bath at 85° C. The heating was stopped, and the reaction solution was cooled naturally and stirred overnight.

The reaction solution was continued to be stirred for 2 hours in an ice bath and filtered under reduced pressure. The filter cake was washed with isopropanol (100 ml×5). Next, the filter cake was dried in the air at room temperature for 2 hours and then at 45° C. in vacuo to give 2-[1-(2-methoxyethyl)-piperidin-4-ylidene]acetic acid hydrochloride (254.5 g).

In some embodiments, N-[4-(3-chloro-4-fluorophenylamino)-7-(2-methoxyethoxy)quinazolin-6-yl]-2-[1-(2-methoxyethyl)piperidin-4-ylidene]acetamide was reacted with an acid to give its corresponding pharmaceutically acceptable salt.

The illustrative examples of acid which can be used in the present application to prepare the pharmaceutically acceptable salt of N-[4-(3-chloro-4-fluorophenylamino)-7-(2-methoxyethoxy)quinazolin-6-yl]-2-[1-(2-methoxyethyl)piperidin-4-ylidene]acetamide include, but are not limited to, hydrochloric acid, hydrobromic acid, sulfuric acid, nitric acid, phosphoric acid, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid and undecylenic acid.

A further aspect of the present application relates to a method for the treatment or prevention of a disease associated with protein kinase, comprising administering to a subject in need thereof a therapeutically or prophylactically effective amount of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof.

In some embodiments, the disease is a cancer.

The illustrative examples of cancer which can be treated or prevented by using the method of the present application include, but are not limited to, breast cancer, head and neck cancer, lung cancer (including non-small cell lung cancer, small cell lung cancer), colon cancer, pancreatic cancer, esophagus cancer, stomach cancer and prostate cancer.

In some embodiments, the subject is a mammal.
In some embodiments, the mammal is a human.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 0.1 mg-1000 mg, which is used as the therapeutically or prophylactically effective amount to treat or prevent the disease associated with protein kinase.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 1 mg-1000 mg, which is used as the therapeutically or prophylactically effective amount to treat or prevent the disease associated with protein kinase.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 10 mg-500 mg, which is used as the therapeutically or prophylactically effective amount to treat or prevent the disease associated with protein kinase.

Yet another aspect of the present application relates to a method for the treatment or prevention of physiological abnormality caused by over-expression of protein tyrosine phosphorylation enzyme in mammal, comprising administering to a mammal in need thereof a therapeutically or prophylactically effective amount of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof.

In some embodiments, the physiological abnormality is caused by the over-expression of EGFR or Her-2.

In some embodiments, the physiological abnormality is cancer.

The illustrative examples of cancer which can be treated or prevented by using the method of the present application include, but are not limited to, breast cancer, head and neck cancer, lung cancer (including non-small cell lung cancer, small cell lung cancer), colon cancer, pancreatic cancer, esophagus cancer, stomach cancer and prostate cancer.

In some embodiments, the mammal is a human.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 0.1 mg-1000 mg, which is used as the therapeutically or prophylactically effective amount to treat or prevent physiological abnormality caused by over-expression of protein tyrosine phosphorylation enzyme in mammal.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 1 mg-1000 mg, which is used as the therapeutically or prophylactically effective amount to treat or prevent physiological abnormality caused by over-expression of protein tyrosine phosphorylation enzyme in mammal.

In some embodiments, a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient is 10 mg-500 mg, which is used as the therapeutically or prophylactically effective amount to treat or prevent physiological abnormality caused by over-expression of protein tyrosine phosphorylation enzyme in mammal.

Another aspect of the present application relates to use of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof in the manufacture of a medicament for the treatment or prevention of a disease associated with protein kinase, preferably in the manufacture of a medicament for the treatment or prevention of physiological abnormality caused by over-expression of protein tyrosine phosphorylation enzyme in mammal.

In some embodiments, N-[4-(3-chloro-4-fluorophenylamino)-7-(2-methoxyethoxy)quinazolin-6-yl]-2-[1-(2-methoxyethyl)piperidin-4-ylidene]acetamide or pharmaceutically acceptable salts thereof is used in the treatment or prevention of the physiological abnormality caused by the over-expression of EGFR and/or Her-2 in mammal. In some embodiments, the physiological abnormality is particularly caused by the over-expression of EGFR.

In some embodiments, the physiological abnormality caused by over-expression of protein tyrosine phosphorylation enzyme and the disease for which the method of inhibiting the activity of protein tyrosine phosphorylation enzyme is effective, are cancer.

The illustrative examples of cancer which can be treated or prevented by using N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof of the present application include, but are not limited to, breast cancer, head and neck cancer, lung cancer (including non-small cell lung cancer, small cell lung cancer), colon cancer, pancreatic cancer, esophagus cancer, stomach cancer, skin cancer, colon cancer, kidney cancer, bladder cancer, ovarian cancer, oral cancer, laryngeal cancer, cervical cancer, liver cancer and prostate cancer.

In some embodiments, the mammal is a human.

In some embodiments, N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof with a unit dose of about 0.1 mg to about 1000 mg is administered to treat or prevent a disease associated with protein kinase, preferably to treat or prevent physiological abnormality caused by over-expression of protein tyrosine phosphorylation enzyme in mammal. If no special indication, all the unit usage doses described in the present application refer to: a unit which can be administered to a patient and is easy to operate and package, i.e., a single dose.

In some embodiments, N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof with a unit dose of about 1 mg to about 1000 mg is administered to treat or prevent a disease associated with protein kinase, preferably to treat or prevent physiological abnormality caused by over-expression of protein tyrosine phosphorylation enzyme in mammal.

In some embodiments, N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof with a unit dose of about 10 mg to about 500 mg is administered to treat or prevent a disease associated with protein kinase, preferably to treat or prevent physiological abnormality caused by over-expression of protein tyrosine phosphorylation enzyme in mammal.

Yet another aspect of the present application relates to use of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof in the manufacture of a medicament for the treatment or prevention of a disease associated with protein kinase, preferably in the manufacture of a medicament for inhibiting the activity of the protein tyrosine phosphorylation enzyme in mammal.

In some embodiments, the mammal is a human.

Another aspect of the present application relates to use of a pharmaceutical composition of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof in the manufacture of a medicament for the treatment or prevention of a disease associated with protein kinase, preferably in the manufacture of a medicament for the treatment or prevention of physiological abnormality caused by over-expression of protein tyrosine phosphorylation enzyme in mammal.

In some embodiments, the pharmaceutical composition of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof is used in the treatment or prevention of physiological abnormality caused by the over-expression of EGFR and/or Her-2 in mammal. In some embodiments, the physiological abnormality is particularly caused by the over-expression of EGFR.

In some embodiments, the physiological abnormality caused by over-expression of protein tyrosine phosphorylation enzyme and the disease for which the method of inhibiting the activity of the protein tyrosine phosphorylation enzyme is effective, are cancer.

The illustrative examples of cancer which can be treated or prevented using the pharmaceutical composition of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof of the present application include, but are not limited to, breast cancer, head and neck cancer, lung cancer (including non-small cell lung cancer, small cell lung cancer), colon cancer, pancreatic cancer, esophagus cancer, stomach cancer, skin cancer, colon cancer, kidney cancer, bladder cancer, ovarian cancer, oral cancer, laryngeal cancer, cervical cancer, liver cancer and prostate cancer.

In some embodiments, the mammal is a human.

In some embodiments, a pharmaceutical composition comprising about 0.1 mg to about 1000 mg of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof is administered as a unit dose to treat or prevent a disease associated with a protein kinase, preferably to inhibit the activity of a protein tyrosine phosphorylation enzyme in mammal.

In some embodiments, a pharmaceutical composition comprising about 1 mg to about 1000 mg of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof is administered as a unit dose to treat or prevent a disease associated with protein kinase, preferably to inhibit the activity of protein tyrosine phosphorylation enzyme in mammal.

In some embodiments, a pharmaceutical composition comprising about 10 mg to about 500 mg of N-[4-(3-chloro-4-fluorophenylamino)-7-(2-methoxyethoxy)quinazolin-6- yl]-2-[1-(2-methoxyethyl)piperidin-4-ylidene]acetamide or a pharmaceutically acceptable salt thereof is administrated as a unit dose to treat or prevent a disease associated with protein kinase, preferably to inhibit the activity of protein tyrosine phosphorylation enzyme in mammal.

Hereinafter, the present disclosure will be described in detail through the examples mentioned below in order to provide a better understanding of the various aspects of the present disclosure and their advantages. However, it should be understood that the examples mentioned below are not limiting and merely used to illustrate some embodiments of the present disclosure.

EXAMPLES

Example 1

N-[4-(3-chloro-4-fluorophenylamino)-7-(2-methoxyethoxy)quinazolin-6-yl]-2-[1-(2-methoxyethyl)piperidin-4-ylidene]acetamide A reaction kettle (20 L) was ventilated with argon gas. 250.0 g (1.062 mol) of 2-[1-(2-methoxyethyl)-piperidin-4-ylidene]acetic acid hydrochloride, 1.46 L of redistilled tetrahydrofuran and 1.46 ml of chromatographically pure N,N-dimethylformamide were added to the reaction kettle, stirred and cooled to 0° C. 128.1 g (1.009 mol, 86.7 ml) of oxalyl chloride was added slowly dropwise, the temperature in the kettle was stably maintained at ≤0° C. during the dropwise addition. After the dropwise addition was completed, the cooling was stopped and the ventilation with argon gas was also stopped. The resulting mixture was stirred at 25° C. for 3 hours, to give a solution of 2-[1-(2-methoxyethyl)-piperidine-4-ylidene]acetyl chloride hydrochloride in tetrahydrofuran.

The reaction kettle containing the solution of 2-[1-(2-methoxyethyl)-piperidin-4-ylidene]acetyl chloride hydrochloride in tetrahydrofuran was ventilated with argon gas, stirred, and cooled to below 0° C. 256.7 g (0.708 mol) of $N^4$-(3-chloro-4-fluorophenyl)-7-(2-methoxyethoxy)quinazolin-4,6-diamine was dissolved in 1.46 L of N-methylpyrrolidone. The solution was slowly added dropwise into the kettle, and the temperature in the kettle was stably maintained at 0° C. or less. After the dropwise addition was completed, the stirring was continued for 1 hour. The cooling was stopped, and the reaction solution was naturally warmed up to 25° C. and stirred overnight.

TLC monitored whether the reaction was completed. After the reaction was completed, the reaction solution was cooled to about 0° C., and 2.9 L of water was slowly added dropwise thereto. The reaction solution in the kettle was transparent. The reaction solution was filtered under reduced pressure to remove residue and then was transferred to a round bottom flask (10 L) in 40° C. water bath under mechanical stirring. 5N sodium hydroxide solution was added dropwise until pH reached about 10, and soon solids were precipitated rapidly. An appropriate amount of water was added so that the reaction system was normally stirred. The water bath was removed, and the reaction solution was stirred at room temperature for 2 hours and filtered under reduced pressure. The filter cake was washed with distilled water until the pH of dropped liquid reached about 7, then dried to give crude product N-[4-(3-chloro-4-fluorophenylamino)-7-(2-methoxyethoxy)quinazolin-6-yl]-2-[1-(2-methoxyethyl) piperidin-4-ylidene]acetamide as a pale pink solid.

20 g of crude product N-[4-(3-chloro-4-fluorophenylamino)-7-(2-methoxyethoxy)quinazolin-6-yl]-2-[1-(2-methoxyethyl)piperidin-4-ylidene]acetamide and 250 ml of isopropanol were added into a kettle (1 L) and mixed under mechanically stirring. The mixture was heated to reflux at 88° C. for 3 hours, and then the heating was stopped and the stirring was maintained overnight. The resulting mixture was filtered under reduced pressure. The filter cake was washed with isopropanol (250 ml×4), filtered under reduced pressure to dryness and dried in the air to give a product N-[4-(3-chloro-4-fluorophenylamino)-7-(2-methoxyethoxy) quinazolin-6-yl]-2-[1-(2-methoxyethyl)piperidin-4-ylidene] acetamide.

Mass Spectrometry (MS) (Instrument Model: 6410B LC-MS; Agilent) showed molecular ion peak of 544.2 ([M+H]$^+$ peak).

Hydrogen Nuclear Magnetic Resonance Spectroscopy showed ($^1$H-NMR) (Instrument Model: VARIAN INOVA 500 MHz; measurement condition: solvent DMSO), the following results were obtained:

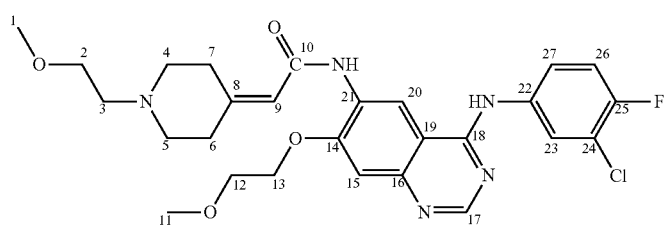

| Serial Number | Chemical Shift δ (ppm) | Multiplicity | Proton Number | Corresponding Proton |
|---|---|---|---|---|
| a | 3.225 | s | 3 | 1 |
| b | 3.42-3.444 | t | 2 | 2 |
| c | 2.488 | s | 4 | 3, 4 |
| d | 2.549 | s | 2 | 5 |
| e | 2.286 | s | 2 | 6 |
| f | 2.995 | s | 2 | 7 |
| g | 6.091 | s | 1 | 9 |
| h | 3.337 | s | 3 | 11 |
| i | 3.777-3.795 | t | 2 | 12 |
| j | 4.333-4.351 | t | 2 | 13 |
| k | 7.292 | s | 1 | 15 |

-continued

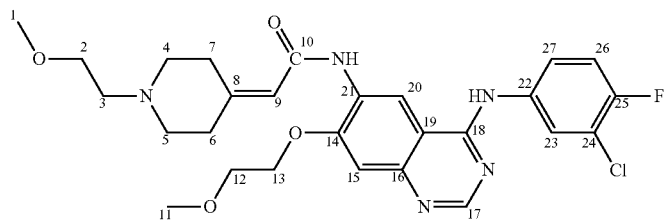

| Serial Number | Chemical Shift δ (ppm) | Multiplicity | Proton Number | Corresponding Proton |
|---|---|---|---|---|
| l | 8.507 | s | 1 | 17 |
| m | 8.853 | s | 1 | 20 |
| n | 8.103-8.121 | m | 1 | 23 |
| o | 7.385-7.421 | t | 1 | 26 |
| P | 7.774-7.806 | m | 1 | 27 |
| q | 9.255 | s | 1 | CONH |
| r | 9.764 | s | 1 | NH |

Carbon Nuclear Magnetic Resonance Spectroscopy showed ($^{13}$C-NMR) (Instrument Model: VARIAN INOVA 500 MHz; measurement condition: solvent DMSO), the following results were obtained:

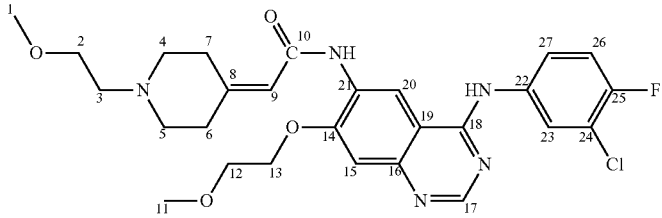

| Serial Number of Carbon Atom | Chemical Shift | Carbon Atom Type |
|---|---|---|
| 1 | 58.695 | $CH_3$ |
| 2 | 70.815 | $CH_2$ |
| 3 | 57.257 | $CH_2$ |
| 4 | 54.911 | $CH_2$ |
| 5 | 55.670 | $CH_2$ |
| 6 | 36.958 | $CH_2$ |
| 7 | 29.397 | $CH_2$ |
| 8 | 156.491 | C |
| 9 | 117.538 | CH |
| 10 | 165.284 | C |
| 11 | 59.000 | $CH_3$ |
| 12 | 70.677 | $CH_2$ |
| 13 | 69.048 | $CH_2$ |
| 14 | 155.217 | C |
| 15 | 108.261 | CH |
| 16 | 149.434 | C |
| 17 | 154.431 | CH |
| 18 | 157.418 | C |
| 19 | 109.653 | C |
| 20 | 116.417 | CH |
| 21 | 128.143 | C |
| 22 | 137.512-137.539 | C |
| 23 | 124.206 | CH |
| 24 | 119.266, 119.415 | C |
| 25 | 152.856, 154.786 | C |
| 26 | 117.016, 117.187 | CH |
| 27 | 123.058-123.112 | CH |

Example 2

N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate 290.0 g of N-[4-(3-chloro-4-fluorophenylamino)-7-(2-methoxyethoxy)quinazolin-6-yl]-2-[1-(2-methoxyethyl)piperidin-4-ylidene]acetamide and 4.5 L of isopropanol were added to a reaction kettle (20 L), heated and stirred at 40° C.

A mixed solution of distilled water (135 ml) and methylsulfonic acid (128.1 g) was slowly added dropwise into the kettle, and the reaction solution in the kettle was clear. After the dropwise addition was completed, the stirring was continued for another 5 min and then stopped, and the reaction solution was drawn off and filtered. The kettle was washed with a mixed solution (150 ml) of water:isopropanol=3:100 (volume ratio), and the washed solution was mixed into the reaction solution. The resulting solution was filtered under reduced pressure to remove residue, and the filtrate was transferred to a round bottom flask (10 L). Then the filter flask was washed with a mixed solution (150 ml) of water:isopropanol=3:100 (volume ratio), and the washed solution was incorporated into the round bottom flask and stirred overnight at room temperature. Solids were precipitated. A filtration in vacuo was carried out. The filter cake was washed with isopropanol (250 ml×4), filtered under reduced pressure to dryness and dried in vacuo at 35° C. for 24 hours to give N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate (356.1 g). Yield: 90.7%.

Mass Spectrometry (MS) detection (Instrument Model: 6410B LC-MS; Agilent), MS: [M+H]$^+$ peak at 544.1.

Hydrogen Nuclear Magnetic Resonance Spectroscopy ($^1$H-NMR) (Instrument Model: VARIAN INOVA 500 MHz; measurement condition: solvent D$_2$O) showed the following results were obtained:

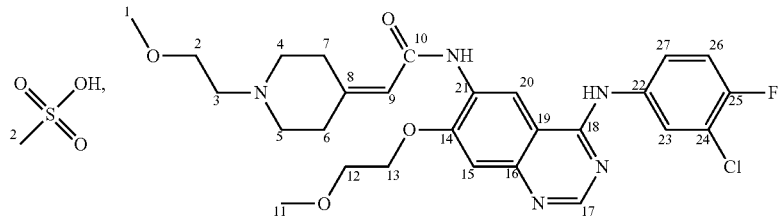

| Serial Number | Chemical Shift δ (ppm) | Multiplicity | Proton Number | Corresponding Proton |
|---|---|---|---|---|
| a | 3.318 | s | 3 | 1 |
| b | 3.694-3.703 | d | 2 | 2 |
| c | 3.302 | s | 2 | 3 |
| d | 2.941 | t | 1 | 4 |
|  | 3.588 | s | 1 |  |
| e | 3.024 | t | 1 | 5 |
|  | 3.610 | s | 1 |  |
| f | 2.497 | s | 1 | 6 |
|  | 2.596-2.619 | d | 1 |  |
| g | 2.522 | s | 1 | 7 |
|  | 3.659 | s | 1 |  |
| h | 5.977 | s | 1 | 9 |
| i | 3.390 | s | 3 | 11 |
| J | 3.813 | s | 2 | 12 |
| k | 4.183 | s | 2 | 13 |
| l | 8.271 | s | 1 | 15 |
| m | 8.341 | s | 1 | 17 |
| n | 6.835 | s | 1 | 20 |
| o | 7.443-7.456 | t | 1 | 23 |
| P | 6.930-6.965 | t | 1 | 26 |
| q | 7.186-7.203 | t | 1 | 27 |
| r | 2.674 | s | 6 | methyl of methylsulfonic acid |

Carbon Nuclear Magnetic Resonance Spectroscopy ($^{13}$C-NMR) (Instrument Model: VARIAN INOVA 500 MHz; measurement condition: solvent D$_2$O) showed the following results were obtained:

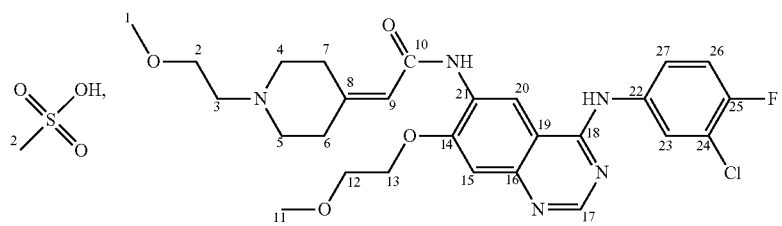

| Serial Number of Carbon Atom | Chemical Shift | Carbon Atom Type |
|---|---|---|
| 1 | 58.550 | $CH_3$ |
| 2 | 65.501 | $CH_2$ |
| 3 | 55.754 | $CH_2$ |
| 4 | 52.671 | $CH_2$ |
| 5 | 53.102 | $CH_2$ |
| 6 | 32.308 | $CH_2$ |
| 7 | 25.647 | $CH_2$ |
| 8 | 149.720 | C |
| 9 | 119.160 | CH |
| 10 | 165.849 | C |
| 11 | 58.420 | $CH_3$ |
| 12 | 69.712 | $CH_2$ |
| 13 | 69.128 | $CH_2$ |
| 14 | 129.254 | C |
| 15 | 112.030 | CH |
| 16 | 136.322 | C |
| 17 | 149.018 | CH |
| 18 | 157.315 | C |
| 19 | 155.129 | C |
| 20 | 99.807 | CH |
| 21 | 106.510 | C |
| 22 | 132.862, 132.889 | C |
| 23 | 124.607 | CH |
| 24 | 120.228, 120.377 | C |
| 25 | 154.424, 156.396 | C |
| 26 | 116.672, 116.848 | CH |
| 27 | 122.944, 123.005 | CH |
| methyl of methylsulfonic acid | 38.648 | $CH_3$ |

Example 3

N-[4-(3-chloro-4-fluorophenylamino)-7-(2-methoxyethoxy)quinazolin-6-yl]-2-[1-(2-methoxyethyl)piperidin-4-ylidene]acetamide disulfate 10 g of N-[4-(3-chloro-4-fluorophenylamino)-7-(2-methoxyethoxy)quinazolin-6-yl]-2-[1-(2-methoxyethyl)piperidin-4-ylidene]acetamide and 155 mL of isopropanol were added to a glass bottle (500 mL), heated and stirred at 40° C.

A mixture of distilled water (5 ml) and concentrated sulfuric acid (3.3 ml) was slowly added dropwise into the glass bottle. The reaction solution in the glass bottle was clear. After the dropwise addition was completed, the stirring was continued for another 5 min and then stopped. The reaction solution was drawn off and filtered. The glass bottle was washed with a mixed solution (5 ml) of water:isopropanol=3:100 (volume ratio), and the washed solution was mixed into the reaction solution. The resulting solution was filtered under reduced pressure to remove residue, and the filtrate was transferred to a round bottom flask (500 ml). Then the filter flask was washed with a mixed solution (5 ml) of water:isopropanol=3:100 (volume ratio), and the washed solution was incorporated into the round bottom flask and stirred overnight at room temperature. Solids were precipitated. A filtration in vacuo was carried out. The filter cake was washed with isopropanol (155 ml×4), filtered under reduced pressure to dryness and dried in vacuo at 35° C. for 24 hours to give N-[4-(3-chloro-4-fluorophenylamino)-7-(2-methoxyethoxy)quinazolin-6-yl]-2-[1-(2-methoxyethyl)piperidin-4-ylidene]acetamide disulfate.

Mass Spectrometry (MS) detection (Instrument Model: 6410B LC-MS; Agilent), MS: [M+H-196]$^+$ peak at 544.

Example 4-24

Salts of N-[4-(3-chloro-4-fluorophenylamino)-7-(2-methoxyethoxy)quinazolin-6-yl]-2-[1-(2-methoxyethyl)piperidin-4-ylidene]acetamide with other acids N-[4-(3-chloro-4-fluorophenylamino)-7-(2-methoxyethoxy)quinazolin-6-yl]-2-[1-(2-methoxyethyl)piperidin-4-ylidene]acetamide was separately reacted with hydrochloric acid, hydrobromic acid, nitric acid, phosphoric acid, acetic acid, benzenesulfonic acid, fumaric acid, maleic acid, nicotinic acid, oleic acid, oxalic acid, propionic acid, salicylic acid, 4-aminosalicylic acid, acetosalicylic acid, tartaric acid, p-toluenesulfonic acid, citric acid, malic acid, naphthalene-1,5-disulfonic acid, sebacic acid, L-aspartic acid, according to the preparation process of Example 2, to give the following products:

| Ex. | Compound |
|---|---|
| 4 | N-[4-(3-chloro-4-fluorophenylamino)-7-(2-methoxyethoxy)quinazolin-6-yl]-2-[1-(2-methoxyethyl)piperidin-4-ylidene]acetamide dihydrochloride |
| 5 | N-[4-(3-chloro-4-fluorophenylamino)-7-(2-methoxyethoxy)quinazolin-6-yl]-2-[1-(2-methoxyethyl)piperidin-4-ylidene]acetamide dihydrobromide |
| 6 | N-[4-(3-chloro-4-fluorophenylamino)-7-(2-methoxyethoxy)quinazolin-6-yl]-2-[1-(2-methoxyethyl)piperidin-4-ylidene]acetamide dinitrate |
| 7 | N-[4-(3-chloro-4-fluorophenylamino)-7-(2-methoxyethoxy)quinazolin-6-yl]-2-[1-(2-methoxyethyl)piperidin-4-ylidene]acetamide diphosphate |
| 8 | N-[4-(3-chloro-4-fluorophenylamino)-7-(2-methoxyethoxy)quinazolin-6-yl]-2-[1-(2-methoxyethyl)piperidin-4-ylidene]acetamide diacetate |
| 9 | N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate |
| 10 | N-[4-(3-chloro-4-fluorophenylamino)-7-(2-methoxyethoxy)quinazolin-6-yl]-2-[1-(2-methoxyethyl)piperidin-4-ylidene]acetamide difumarate |
| 11 | N-[4-(3-chloro-4-fluorophenylamino)-7-(2-methoxyethoxy)quinazolin-6-yl]-2-[1-(2-methoxyethyl)piperidin-4-ylidene]acetamide dimaleate |
| 12 | N-[4-(3-chloro-4-fluorophenylamino)-7-(2-methoxyethoxy)quinazolin-6-yl]-2-[1-(2-methoxyethyl)piperidin-4-ylidene]acetamide dinicotinate |
| 13 | N-[4-(3-chloro-4-fluorophenylamino)-7-(2-methoxyethoxy)quinazolin-6-yl]-2-[1-(2-methoxyethyl)piperidin-4-ylidene]acetamide dioleate |
| 14 | N-[4-(3-chloro-4-fluorophenylamino)-7-(2-methoxyethoxy)quinazolin-6-yl]-2-[1-(2-methoxyethyl)piperidin-4-ylidene]acetamide dioxalate |
| 15 | N-[4-(3-chloro-4-fluorophenylamino)-7-(2-methoxyethoxy)quinazolin-6-yl]-2-[1-(2-methoxyethyl)piperidin-4-ylidene]acetamide dipropionate |
| 16 | N-[4-(3-chloro-4-fluorophenylamino)-7-(2-methoxyethoxy)quinazolin-6-yl]-2-[1-(2-methoxyethyl)piperidin-4-ylidene]acetamide disalicylate |
| 17 | N-[4-(3-chloro-4-fluorophenylamino)-7-(2-methoxyethoxy)quinazolin-6-yl-2-[1-(2-methoxyethyl)piperidin-4-ylidene]acetamide bis(4-aminosalicylate) |
| 18 | N-[4-(3-chloro-4-fluorophenylamino)-7-(2-methoxyethoxy)quinazolin-6-yl]-2-[1-(2-methoxyethyl)piperidin-4-ylidene]acetamide diacetylsalicylate |
| 19 | N-[4-(3-chloro-4-fluorophenylamino)-7-(2-methoxyethoxy)quinazolin-6-yl]-2-[1-(2-methoxyethyl)piperidin-4-ylidene]acetamide ditartrate |
| 20 | N-[4-(3-chloro-4-fluorophenylamino)-7-(2-methoxyethoxy)quinazolin-6-yl]-2-[1-(2-methoxyethyl)piperidin-4-ylidene]acetamide di(p-toluenesulfonate) |
| 21 | N-[4-(3-chloro-4-fluorophenylamino)-7-(2-methoxyethoxy)quinazolin-6-yl]-2-[1-(2-methoxyethyl)piperidin-4-ylidene]acetamide dicitrate |
| 22 | N-[4-(3-chloro-4-fluorophenylamino)-7-(2-methoxyethoxy)quinazolin-6-yl]-2-[1-(2-methoxyethyl)piperidin-4-ylidene]acetamide dimalate |
| 23 | N-[4-(3-chloro-4-fluorophenylamino)-7-(2-methoxyethoxy)quinazolin-6-yl]-2-[1-(2-methoxyethyl)piperidin-4-ylidene]acetamide bis(naphthalene-1,5-disulfonate) |
| 24 | N-[4-(3-chloro-4-fluorophenylamino)-7-(2-methoxyethoxy)quinazolin-6-yl]-2-[1-(2-methoxyethyl)piperidin-4-ylidene]acetamide bis(decanedioate) |
| 25 | N-[4-(3-chloro-4-fluorophenylamino)-7-(2-methoxyethoxy)quinazolin-6-yl]-2-[1-(2-methoxyethyl)piperidin-4-ylidene]acetamide bis(L-aspartate) |

The following $^1$H NMR data of compound 4 to compound 25 were obtained by Bruker AV400 and D$_2$O as solvent:

N-[4-(3-chloro-4-fluorophenylamino)-7-(2-methoxyethoxy)quinazolin-6-yl]-2-[1-(2-methoxyethyl)piperidin-4-ylidene]acetamide dihydrochloride 2.50 (s, 1H), 2.52 (s, 1H), 2.61 (d, 1H), 2.94 (t, 1H), 3.02 (t, 1H), 3.30 (s, 2H), 3.32 (s, 3H), 3.39 (s, 3H), 3.59 (s, 1H), 3.61 (s, 1H), 3.66 (s, 1H), 3.69 (d, 2H), 3.81 (s, 2H), 4.18 (s, 2H), 5.98 (s, 1H), 6.84 (s, 1H), 6.95 (t, 1H), 7.20 (t, 1H), 7.45 (t, 1H), 8.27 (s, 1H), 8.34 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide dihydrobromide 2.48 (s, 1H), 2.53 (s, 1H), 2.63 (d, 1H), 2.90 (t, 1H), 3.00 (t, 1H), 3.31 (s, 2H), 3.35 (s, 3H), 3.37 (s, 3H), 3.55 (s, 1H), 3.62 (s, 1H), 3.64 (s, 1H), 3.67 (d, 2H), 3.85 (s, 2H), 4.15 (s, 2H), 5.94 (s, 1H), 6.80 (s, 1H), 6.97 (t, 1H), 7.25 (t, 1H), 7.49 (t, 1H), 8.31 (s, 1H), 8.38 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide dinitrate 2.49 (s, 1H), 2.54 (s, 1H), 2.62 (d, 1H), 2.93 (t, 1H), 3.03 (t, 1H), 3.33 (s, 2H), 3.36 (s, 3H), 3.38 (s, 3H), 3.54 (s, 1H), 3.67 (s, 1H), 3.69 (s, 1H), 3.70 (d, 2H), 3.88 (s, 2H), 4.16 (s, 2H), 5.97 (s, 1H), 6.83 (s, 1H), 6.96 (t, 1H), 7.23 (t, 1H), 7.46 (t, 1H), 8.33 (s, 1H), 8.36 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide diphosphate 2.52 (s, 1H), 2.56 (s, 1H), 2.66 (d, 1H), 2.95 (t, 1H), 3.02 (t, 1H), 3.35 (s, 2H), 3.36 (s, 3H), 3.39 (s, 3H), 3.54 (s, 1H), 3.65 (s, 1H), 3.69 (s, 1H), 3.72 (d, 2H), 3.88 (s, 2H), 4.16 (s, 2H), 5.98 (s, 1H), 6.83 (s, 1H), 6.91 (t, 1H), 7.23 (t, 1H), 7.48 (t, 1H), 8.30 (s, 1H), 8.38 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide diacetate 2.08 (s, 6H), 2.54 (s, 1H), 2.56 (s, 1H), 2.69 (d, 1H), 2.95 (t, 1H), 3.07 (t, 1H), 3.35 (s, 2H), 3.36 (s, 3H), 3.37 (s, 3H), 3.54 (s, 1H), 3.62 (s, 1H), 3.69 (s, 1H), 3.74 (d, 2H), 3.88 (s, 2H), 4.16 (s, 2H), 5.99 (s, 1H), 6.83 (s, 1H), 6.91 (t, 1H), 7.26 (t, 1H), 7.44 (t, 1H), 8.30 (s, 1H), 8.39 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate 2.51 (s, 1H), 2.56 (s, 1H), 2.60 (d, 1H), 2.94 (t, 1H), 3.07 (t, 1H), 3.32 (s, 2H), 3.36 (s, 3H), 3.39 (s, 3H), 3.54 (s, 1H), 3.62 (s, 1H), 3.70 (s, 1H), 3.74 (d, 2H), 3.85 (s, 2H), 4.16 (s, 2H), 6.01 (s, 1H), 6.83 (s, 1H), 6.93 (t, 1H), 7.27 (t, 1H), 7.31-7.42 (m, 2H), 7.46 (t, 1H), 7.54-7.93 (m, 8H), 8.32 (s, 1H), 8.35 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide difumarate 2.53 (s, 1H), 2.55 (s, 1H), 2.60 (d, 1H), 2.95 (t, 1H), 3.07 (t, 1H), 3.33 (s, 2H), 3.36 (s, 3H), 3.39 (s, 3H), 3.54 (s, 1H), 3.67 (s, 1H), 3.71 (s, 1H), 3.74 (d, 2H), 3.86 (s, 2H), 4.18 (s, 2H), 6.03 (s, 1H), 6.83 (s, 1H), 6.95 (t, 1H), 6.96 (s, 2H), 7.04 (s, 2H), 7.28 (t, 1H), 7.47 (t, 1H), 8.32 (s, 1H), 8.38 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide dimaleate 2.50 (s, 1H), 2.57 (s, 1H), 2.61 (d, 1H), 2.97 (t, 1H), 3.08 (t, 1H), 3.34 (s, 2H), 3.37 (s, 3H), 3.39 (s, 3H), 3.54 (s, 1H), 3.66 (s, 1H), 3.71 (s, 1H), 3.77 (d, 2H), 3.86 (s, 2H), 4.18 (s, 2H), 6.02 (s, 1H), 6.28 (s, 2H), 6.30 (s, 2H), 6.84 (s, 1H), 6.95 (t, 1H), 7.26 (t, 1H), 7.44 (t, 1H), 8.33 (s, 1H), 8.39 (s, 1H).

N-[4-(3-chloro-4-fluorophenylamino)-7-(2-methoxyethoxy)quinazolin-6-yl]-2-[1-(2-methoxyethyl)piperidin-4-ylidene]acetamide dinicotinate 2.47 (s, 1H), 2.52 (s, 1H), 2.62 (d, 1H), 2.94 (t, 1H), 3.06 (t, 1H), 3.38 (s, 2H), 3.39 (s, 3H), 3.40 (s, 3H), 3.56 (s, 1H), 3.67 (s, 1H), 3.68 (s, 1H), 3.70 (d, 2H), 3.85 (s, 2H), 4.16 (s, 2H), 5.94 (s, 1H), 6.83 (s, 1H), 6.95 (t, 1H), 7.23 (t, 1H), 7.43 (t, 1H), 7.50 (m, 2H), 8.17 (m, 2H), 8.32 (s, 1H), 8.38 (s, 1H), 8.79 (m, 2H), 9.04 (m, 2H).

N-[4-(3-chloro-4-fluorophenylamino)-7-(2-methoxyethoxy)quinazolin-6yl]-2-[1-(2-methoxyethyl)piperidin-4-ylidene]acetamide dioleate 0.96 (t, 6H), 1.27-1.31 (m, 28H), 1.33-1.35 (m, 12H), 1.53-1.58 (m, 4H), 1.94-1.98 (m, 8H), 2.23 (t, 4H), 2.49 (s, 1H), 2.53 (s, 1H), 2.61 (d, 1H), 2.93 (t, 1H), 3.01 (t, 1H), 3.34 (s, 2H), 3.36 (s, 3H), 3.39 (s, 3H), 3.55 (s, 1H), 3.65 (s, 1H), 3.68 (s, 1H), 3.71 (d, 2H), 3.88 (s, 2H), 4.17 (s, 2H), 5.41 (s, 2H), 5.45 (s, 2H), 5.98 (s, 1H), 6.83 (s, 1H), 6.95 (t, 1H), 7.23 (t, 1H), 7.45 (t, 1H), 8.32 (s, 1H), 8.37 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide dioxalate 2.48 (s, 1H), 2.52 (s, 1H), 2.62 (d, 1H), 2.95 (t, 1H), 3.03 (t, 1H), 3.35 (s, 2H), 3.36 (s, 3H), 3.37 (s, 3H), 3.56 (s, 1H), 3.67 (s, 1H), 3.69 (s, 1H), 3.72 (d, 2H), 3.88 (s, 2H), 4.16 (s, 2H), 5.99 (s, 1H), 6.83 (s, 1H), 6.93 (t, 1H), 7.24 (t, 1H), 7.46 (t, 1H), 8.30 (s, 1H), 8.38 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide dipropionate 1.09 (t, 6H), 2.27 (q, 4H), 2.45 (s, 1H), 2.57 (s, 1H), 2.65 (d, 1H), 2.95 (t, 1H), 3.05 (t, 1H), 3.32 (s, 2H), 3.36 (s, 3H), 3.39 (s, 3H), 3.56 (s, 1H), 3.67 (s, 1H), 3.69 (s, 1H), 3.70 (d, 2H), 3.88 (s, 2H), 4.16 (s, 2H), 6.01 (s, 1H), 6.84 (s, 1H), 6.93 (t, 1H), 7.25 (t, 1H), 7.46 (t, 1H), 8.31 (s, 1H), 8.37 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide disalicylate 2.47 (s, 1H), 2.59 (s, 1H), 2.65 (d, 1H), 2.94 (t, 1H), 3.05 (t, 1H), 3.31 (s, 2H), 3.36 (s, 3H), 3.39 (s, 3H), 3.55 (s, 1H), 3.67 (s, 1H), 3.68 (s, 1H), 3.72 (d, 2H), 3.85 (s, 2H), 4.16 (s, 2H), 6.03 (s, 1H), 6.84 (s, 1H), 6.97 (t, 1H), 6.95-7.04 (m, 4H), 7.23 (t, 1H), 7.46 (t, 1H), 7.48-7.96 (m, 4H), 8.30 (s, 1H), 8.38 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide bis(4-aminosalicylate)

2.50 (s, 1H), 2.61 (s, 1H), 2.66 (d, 1H), 2.93 (t, 1H), 3.05 (t, 1H), 3.32 (s, 2H), 3.36 (s, 3H), 3.37 (s, 3H), 3.58 (s, 1H), 3.67 (s, 1H), 3.69 (s, 1H), 3.75 (d, 2H), 3.85 (s, 2H), 4.16 (s, 2H), 6.05 (s, 1H), 6.11-6.24 (m, 4H), 6.88 (s, 1H), 6.98 (t, 1H), 7.25 (t, 1H), 7.47 (t, 1H), 7.68-7.74 (m, 2H), 8.34 (s, 1H), 8.36 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide diacetylsalicylate 2.11 (s, 6H), 2.49 (s, 1H), 2.51 (s, 1H), 2.65 (d, 1H), 2.92 (t, 1H), 3.03 (t, 1H), 3.31 (s, 2H), 3.34 (s, 3H), 3.39 (s, 3H), 3.57 (s, 1H), 3.67 (s, 1H), 3.68 (s, 1H), 3.75 (d, 2H), 3.89 (s, 2H), 4.17 (s, 2H), 6.03 (s, 1H), 6.82 (s, 1H), 6.98 (t, 1H), 7.27 (t, 1H), 7.21-7.30 (m, 4H), 7.42 (t, 1H), 7.78-8.09 (m, 4H), 8.31 (s, 1H), 8.36 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide ditartrate 2.53 (s, 1H), 2.56 (s, 1H), 2.61 (d, 1H), 2.97 (t, 1H), 3.05 (t, 1H), 3.33 (s, 2H), 3.37 (s, 3H), 3.39 (s, 3H), 3.54 (s, 1H), 3.69 (s, 1H), 3.71 (s, 1H), 3.75 (d, 2H), 3.91 (s, 2H), 4.18 (s, 2H), 4.51 (s, 4H), 5.99 (s, 1H), 6.82 (s, 1H), 6.98 (t, 1H), 7.23 (t, 1H), 7.48 (t, 1H), 8.31 (s, 1H), 8.38 (s, 1H).

N-[4-(3-chloro-4-fluorophenylamino)-7-(2-methoxyethoxy)quinazolin-6yl]-2-[1-(2-methoxyethyl)piperidin-4-ylidene]acetamide di(p-toluenesulfonate)

2.33 (s, 6H), 2.50 (s, 1H), 2.52 (s, 1H), 2.61 (d, 1H), 2.91 (t, 1H), 3.05 (t, 1H), 3.30 (s, 2H), 3.31 (s, 3H), 3.35 (s, 3H), 3.57 (s, 1H), 3.63 (s, 1H), 3.71 (s, 1H), 3.74 (d, 2H), 3.86 (s, 2H), 4.16 (s, 2H), 6.05 (s, 1H), 6.84 (s, 1H), 6.91 (t, 1H), 7.25 (t, 1H), 7.31-7.42 (m, 4H), 7.45 (t, 1H), 7.74-7.93 (m, 4H), 8.31 (s, 1H), 8.37 (s, 1H).

N-[4-(3-chloro-4-fluorophenylamino)-7-(2-methoxy-ethoxy)quinazolin-6yl]-2-[1-(2-methoxyethyl)piperidin-4-ylidene]acetamide dicitrate 2.47 (s, 1H), 2.50 (s, 1H), 2.60 (d, 1H), 2.64 (s, 8H), 2.92 (t, 1H), 3.05 (t, 1H), 3.31 (s, 2H), 3.35 (s, 3H), 3.37 (s, 3H), 3.59 (s, 1H), 3.62 (s, 1H), 3.75 (s, 1H), 3.78 (d, 2H), 3.88 (s, 2H), 4.11 (s, 2H), 6.02 (s, 1H), 6.85 (s, 1H), 6.90 (t, 1H), 7.24 (t, 1H), 7.45 (t, 1H), 8.31 (s, 1H), 8.41 (s, 1H).

N-[4-(3-chloro-4-fluorophenylamino)-7-(2-methoxy-ethoxy)quinazolin-6yl]-2-[1-(2-methoxyethyl)piperidin-4-ylidene]acetamide dimalate 2.47 (s, 1H), 2.53 (q, 2H), 2.56 (s, 1H), 2.63 (d, 1H), 2.78 (q, 2H), 2.95 (t, 1H), 3.04 (t, 1H), 3.35 (s, 2H), 3.38 (s, 3H), 3.39 (s, 3H), 3.53 (s, 1H), 3.69 (s, 1H), 3.71 (s, 1H), 3.73 (d, 2H), 3.85 (s, 2H), 4.12 (s, 2H), 4.42 (q, 2H), 5.92 (s, 1H), 6.85 (s, 1H), 6.92 (t, 1H), 7.22 (t, 1H), 7.47 (t, 1H), 8.33 (s, 1H), 8.43 (s, 1H).

N-[4-(3-chloro-4-fluorophenylamino)-7-(2-methoxy-ethoxy)quinazolin-6yl]-2-[1-(2-methoxyethyl)piperidin-4-ylidene]acetamide bis(naphthalene-1,5-disulfonate)

2.48 (s, 1H), 2.58 (s, 1H), 2.62 (d, 1H), 2.97 (t, 1H), 3.00 (t, 1H), 3.33 (s, 2H), 3.37 (s, 3H), 3.38 (s, 3H), 3.54 (s, 1H), 3.66 (s, 1H), 3.77 (s, 1H), 3.79 (d, 2H), 3.88 (s, 2H), 4.10 (s, 2H), 5.95 (s, 1H), 6.80 (s, 1H), 6.93 (t, 1H), 7.24 (t, 1H), 7.48 (t, 1H), 7.63-7.98 (m, 12H), 8.30 (s, 1H), 8.40 (s, 1H).

N-[4-(3-chloro-4-fluorophenylamino)-7-(2-methoxy-ethoxy)quinazolin-6yl]-2-[1-(2-methoxyethyl)piperidin-4-ylidene]acetamide bis(decanedioate)

1.27-1.31 (m, 16H), 1.54-1.58 (m, 8H), 2.23 (t, 8H), 2.54 (s, 1H), 2.61 (s, 1H), 2.65 (d, 1H), 2.94 (t, 1H), 3.02 (t, 1H), 3.32 (s, 2H), 3.36 (s, 3H), 3.39 (s, 3H), 3.53 (s, 1H), 3.67 (s, 1H), 3.78 (s, 1H), 3.81 (d, 2H), 3.85 (s, 2H), 4.13 (s, 2H), 5.97 (s, 1H), 6.83 (s, 1H), 6.93 (t, 1H), 7.22 (t, 1H), 7.46 (t, 1H), 8.32 (s, 1H), 8.42 (s, 1H).

N-[4-(3-chloro-4-fluorophenylamino)-7-(2-methoxy-ethoxy)quinazolin-6yl]-2-[1-(2-methoxyethyl)piperidin-4-ylidene]acetamide bis(L-aspartate)

2.50 (s, 1H), 2.60 (q, 2H), 2.58 (s, 1H), 2.67 (d, 1H), 2.85 (q, 2H), 2.97 (t, 1H), 3.04 (t, 1H), 3.32 (s, 2H), 3.35 (s, 3H), 3.37 (s, 3H), 3.55 (s, 1H), 3.68 (s, 1H), 3.75 (s, 1H), 3.73 (d, 2H), 3.82 (q, 2H), 3.87 (s, 2H), 4.14 (s, 2H), 5.97 (s, 1H), 6.88 (s, 1H), 6.91 (t, 1H), 7.2 (t, 1H), 7.48 (t, 1H), 8.34 (s, 1H), 8.47 (s, 1H).

The compounds used in the following experimental process and their abbreviations:

Compound 1: N-[4-(3-chloro-4-fluorophenylamino)-7-(2-methoxyethoxy)quinazolin-6yl]-2-[1-(2-methoxyethyl)piperidin-4-ylidene]acetamide;

Compound 2: N-[4-(3-chloro-4-fluorophenylamino)-7-(2-methoxyethoxy)quinazolin-6yl]-2-[1-(2-methoxyethyl)piperidin-4-ylidene]acetamide dihydrochloride;

Compound 3: N-[4-(3-chloro-4-fluorophenylamino)-7-(2-methoxyethoxy)quinazolin-6yl]-2-[1-(2-methoxyethyl)piperidin-4-ylidene]acetamide dimethylsulfonate;

Compound 4: N-[4-(3-chloro-4-fluorophenylamino)-7-(2-methoxyethoxy)quinazolin-6yl]-2-[piperidin-4-ylidene]acetamide dihydrochloride with the following structural formula:

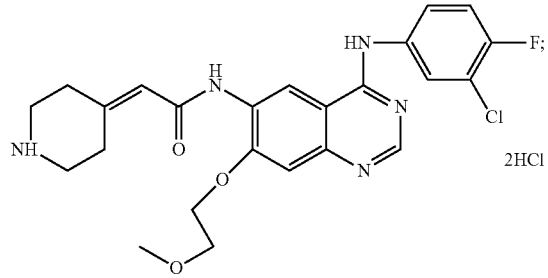 [SMILES: COCCOc1cc2ncnc(Nc3ccc(F)c(Cl)c3)c2cc1NC(=O)C=C1CCNCC1]

Compound 5: N-[4-(3-chloro-4-fluorophenylamino)-7-(2-methoxyethoxy)quinazolin-6yl]-2-[piperidin-4-ylidene]acetamide disulfate;

Compound 6: N-[4-(3-chloro-4-fluorophenylamino)-7-(2-methoxyethoxy)quinazolin-6-yl]-2-[1-(2-methoxyethyl)piperidin-4-ylidene]acetamide dinitrate;

Compound 7: N-[4-(3-chloro-4-fluorophenylamino)-7-(2-methoxyethoxy)quinazolin-6-yl]-2-[1-(2-methoxyethyl)piperidin-4-ylidene]acetamide diphosphate;

Compound 8: N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate;

Compound 9: N-[4-(3-chloro-4-fluorophenylamino)-7-(2-methoxyethoxy)quinazolin-6-yl]-2-[1-(2-methoxyethyl)piperidin-4-ylidene]acetamide difumarate;

Compound 10: N-[4-(3-chloro-4-fluorophenylamino)-7-(2-methoxyethoxy)quinazolin-6-yl]-2-[1-(2-methoxyethyl)piperidin-4-ylidene]acetamide dimaleate;

Compound 11: N-[4-(3-chloro-4-fluorophenylamino)-7-(2-methoxyethoxy)quinazolin-6yl]-2-[1-(2-methoxyethyl)piperidin-4-ylidene]acetamide di(p-toluenesulfonate);

Compound 12: N-[4-(3-ethynylphenylamino-7-(2-ethoxy)quinazolin-6-yl]-2-[1-methylpiperidin-4-ylidene]acetamide dihydrochloride with the following structural formula:

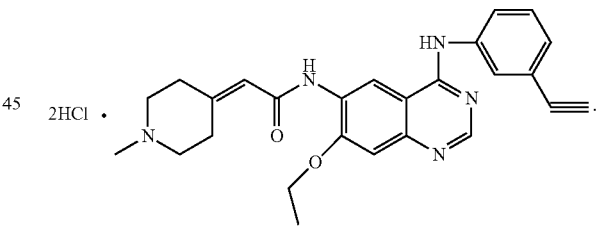

Biological Examples

Biological Example 1

Bioavailability Assay in Rats

Experiment I. Bioavailability Assay for N-[4-(3-chloro-4-fluorophenylamino)-7-(2-methoxyethoxy)quinazolin-6-yl]-2-[1-(2-methoxyethyl)piperidin-4-ylidene]acetamide Dihydrochloride in Rats 1. Experimental Animals:

12 Wistar rats (male, weighing 200-220 g) were purchased from Beijing Vital River Laboratory Animal Technology Co., Ltd. License No.: SCXK (Beijing) 2007-0001.

2. Preparation of Tested Drugs:

2.1 30 mg of N-[4-(3-chloro-4-fluorophenylamino)-7-(2-methoxyethoxy)quinazolin-6-yl]-2-[1-(2-methoxyethyl)piperidin-4-ylidene]acetamide dihydrochloride was weighted, and 6 ml of ultrapure water was added thereto to prepare a sample solution (5 mg/ml)) for use in intravenous administration.

2.2 30 mg of N-[4-(3-chloro-4-fluorophenylamino)-7-(2-methoxyethoxy)quinazolin-6yl]-2-[1-(2-methoxyethyl)piperidin-4-ylidene]acetamide dihydrochloride was weighted, and 12 ml of ultrapure water was added thereto to prepare a sample solution (2.5 mg/ml)) for use in intragastric administration.

3. Experimental Scheme:

| Administration Route | Administration Dose | Drug Concentration | Administration Volume | Number of Animals |
|---|---|---|---|---|
| tail intravenous injection (iv) | 20 mg/kg | 5 mg/ml | 4 ml/kg | 6 |
| intragastric gavage (ig) | 20 mg/kg | 2.5 mg/ml | 8 ml/kg | 6 |

4. Assay Method:

4.1 HPLC/MS Conditions:

4.1.1 HPLC Conditions: chromatographic column: octadecyl-bonded silica gel as filler (4.6 mm×50 mm, 1.8 μm), Agilent; mobile phase: methanol: 5 mM ammonium acetate (PH4.0) (60: 40); flow rate: 1 ml/min; column temperature: 40° C.

4.1.2 MS Conditions:

Source Parameters:

| Gas Temperature | Gas Flow Rate | Sprayer | Capillary Tube Positive Electrode | Capillary Tube Negative Electrode |
|---|---|---|---|---|
| 350° C. | 8 l/min | 35 psi | 4000 V | 4000 V |

MRM Mode Detection

Ion: 544.3→457.1 (N-[4-(3-chloro-4-fluorophenylamino)-7-(2-methoxyethoxy)quinazolin-6-yl]-2-[1-(2-methoxyethyl)piperidin-4-ylidene]acetamide dihydrochloride)

559.3→440.3 (internal standard, atorvastatin hemi-calcium salt)

Dwell Time: 80; fragment voltage: 180; collision energy: 25;

4.2 Establishment of Standard Curve:

1 mg of N-[4-(3-chloro-4-fluorophenylamino)-7-(2-methoxyethoxy)quinazolin-6-yl]-2-[1-(2-methoxyethyl)piperidin-4-ylidene]acetamide dihydrochloride was weighted and formulated into a solution in methanol (1 mg/ml)). The solution was then diluted stepwise into standard solutions of 50 ng/ml, 100 ng/ml, 200 ng/ml, 500 ng/ml, 1 μg/ml, 2 μg/ml, 5 μg/ml, 10 μg/ml, 20 μg/ml, 50 μg/ml, and 100 μg/ml. 10 μl of the standard solutions were separately pipetted into centrifuge tubes (1.5 ml). 10 μl of internal standard (1 μg/ml Lipitor solution in methanol) was added thereto. 100 μl of rat plasma was then added thereto. The mixture was vortexed. Then 200 μl of acetonitrile was added to precipitate protein, then vortexed for 1 min and centrifuged at 16000 r/min for 8 min 10 μl of the supernatant was directly injected for measurement.

4.3 Treatment of Blood Sample:

12 rats were randomly divided into two groups, i.e. six rats per group. These rats were fasted and ad libitum accessed to water for 12 hours before administration. Blank blood (about 0.5 ml) of each rat was withdrawn, and then N-[4-(3-chloro-4-fluorophenylamino)-7-(2-methoxyethoxy)quinazolin-6-yl]-2-[1-(2-methoxyethyl)piperidin-4-ylidene]acetamide dihydrochloride (20 mg/kg) was administrated via intragastric gavage and tail intravenous injection, respectively. Blood (about 0.5 ml) was withdrawn from the orbital venous plexus at different time points after the administration (blood collection points for tail intravenous administration were: 5 min, 15 min, 0.5 h, 1 h, 2 h, 3 h, 4 h, 6 h, 8 h, 12 h, 18 h, 24 h, 30 h; and blood collection time-points for intragastric administration were: 5 min, 10 min, 20 min, 30 min, 45 min, 1 h, 2 h, 3 h, 4 h, 6 h, 8 h, 12 h, 18 h, 24 h, 30 h). The blood was drawn into a heparinized centrifuge tube and centrifuged at 8000 r/min for 10 min 100 μl of the plasma was pipetted into a centrifuge tube (1.5 ml), and 10 μl of internal standard (1 μg/ml atorvastatin hemi-calcium salt solution in methanol) was added thereto. The resulting mixture was vortexed. Then 200 μl of acetonitrile was added to precipitate protein, vortexed for 1 min and centrifuged at 16000 r/min for 8 min The supernatant was recovered, and 10 μl of the supernatant was directly injected for detection.

5. Results 5.1 A standard curve with the natural logarithm of the sample concentration as abscissa and the natural logarithm of the peak area ratio of the sample to the internal standard as ordinate was established as: y=1.008x−4.149; R2=0.998

5.2 Plasma drug concentration (ng/ml) at each time point was shown in the table below:

5.2.1 Results of Intravenous Administration

| Time (h) | Average Plasma Drug Concentration | SD | RSD (%) |
|---|---|---|---|
| 0.083 | 4847.48 | 338.85 | 6.99 |
| 0.25 | 3237.68 | 807.34 | 24.94 |
| 0.5 | 2700.42 | 317.47 | 11.76 |
| 1 | 1722.07 | 277.05 | 16.09 |
| 2 | 1334.35 | 192.82 | 14.45 |
| 3 | 989.19 | 90.78 | 9.18 |
| 4 | 747.58 | 67.33 | 9.01 |
| 6 | 556.90 | 69.34 | 12.45 |
| 8 | 546.62 | 55.57 | 10.17 |
| 12 | 324.63 | 32.99 | 10.16 |
| 18 | 180.70 | 50.20 | 27.78 |
| 24 | 80.80 | 29.73 | 36.80 |
| 30 | 29.63 | 14.12 | 47.65 |
| K (elimination rate constant) | 0.14 | | |
| T½ elimination half-life (h) | 5.18 | | |
| AUC (ng * h/mL) | 12922.47 | | |

5.2.2 Results of Intragastric Administration:

| Time (h) | Average Plasma Drug Concentration | SD | RSD (%) |
|---|---|---|---|
| 0.083 | 17.10 | 7.66 | 44.80 |
| 0.167 | 39.40 | 13.78 | 34.96 |
| 0.33 | 144.94 | 70.65 | 48.74 |
| 0.5 | 202.03 | 91.88 | 45.48 |
| 0.75 | 284.55 | 138.25 | 48.58 |
| 1 | 341.83 | 158.45 | 46.35 |
| 2 | 341.73 | 139.27 | 40.76 |
| 3 | 405.75 | 105.86 | 26.09 |
| 4 | 468.01 | 63.49 | 13.57 |

-continued

| Time (h) | Average Plasma Drug Concentration | SD | RSD (%) |
|---|---|---|---|
| 6 | 535.91 | 97.80 | 18.25 |
| 8 | 495.40 | 152.16 | 30.72 |
| 12 | 329.79 | 80.18 | 24.31 |
| 18 | 138.89 | 49.33 | 35.52 |
| 24 | 72.44 | 52.43 | 72.38 |
| 30 | 22.67 | 10.39 | 45.83 |
| T½ elimination half-life (h) | 4.732 | | |
| AUC (ng * h/mL) | 7349.443 | | |

5.2.3 Conclusion

Method for the calculation of bioavailability:

$$F=(AUC_{ig} \times D_{iv})/(AUC_{iv} \times D_{ig}) \times 100\%$$

wherein D is dose; AUC: the area under the plasma drug concentration-time curve; ig represents intragastric administration; and iv represents intravenous injection administration.

N-[4-(3-chloro-4-fluorophenylamino)-7-(2-methoxyethoxy)quinazolin-6-yl]-2-[1-(2-methoxyethyl)piperidin-4-ylidene]acetamide dihydrochloride has a bioavailability of 56.87%, and has good pharmacokinetic properties.

Experiment II. Bioavailability Assay for N-[4-(3-chloro-4-fluorophenylamino)-7-(2-methoxyethoxy)quinazolin-6-yl]-2-[1-(2-methoxyethyl)piperidin-4-ylidene]acetamide Dihydrobromide in Rats 1. Experimental Animals:

12 Wistar rats (half of them were male and half of them were female, weighting 160-190 g) were purchased from Beijing Vital River Laboratory Animal Technology Co., Ltd. License No.: SCXK (Beijing) 2007-0001.

2. Administration Scheme:

| Administration Route | Administration Dose | Drug Concentration | Administration Volume | Solvent | Number of Animals |
|---|---|---|---|---|---|
| tail intravenous injection (iv) | 20 mg/kg | 4 mg/ml | 5 ml/kg | normal saline | 6 |
| Intragastric gavage (ig) | 20 mg/kg | 4 mg/ml | 5 ml/kg | | 6 |

3. Assay Method:

3.1 Dose Regimens and Handling of Blood Sample:

12 rats were fasted and ad libitum accessed to water for 12 hours before administration. They were randomly divided into two groups, i.e. six rats per group, and were administered the test article according to the administration scheme. Blood (about 0.5 ml) was drawn from the orbital venous plexus before dosing and at 5 min, 15 min, 0.5 h, 1 h, 2 h, 3 h, 4 h, 6 h, 8 h, 10 h, 24 h, 30h after the dosing, and put into a heparinized tube and centrifuged at 8000 r/min for 10 min 100 μl of the plasma was recovered, and 10 μl of internal standard (1 μg/ml atorvastatin hemi-calcium salt solution in methanol) was added thereto. The resulting mixture was vortexed. Then 200 μl of acetonitrile was added to precipitate protein, vortexed for 2 min and centrifuged at 13000 r/min for 10 min The supernatant was obtained, and 20 μl of the supernatant was directly injected for measurement.

3.2 Establishment of Standard Curve:

10 μl of N-[4-(3-chloro-4-fluorophenylamino)-7-(2-methoxyethoxy)quinazolin-6-yl]-2-[1-(2-methoxyethyl)piperidin-4-ylidene]acetamide dihydrobromide solutions in methanol with different concentrations (50 ng/ml, 100 ng/ml, 250 ng/ml, 500 ng/ml, 1 μg/ml, 2.5 μg/ml, 5μg/ml, 10 μg/ml, 25 μg/ml, 50 μg/ml, 100 μg/ml)) were separately pipetted into centrifuge tubes (1.5 ml). 100 μl of rat blank plasma was added thereto and vortexed. 10 μl of internal standard (1 μg/ml atorvastatin hemi-calcium salt solution in methanol) was added. Then 200 μl of acetonitrile was added to precipitate protein, vortexed for 2 min and centrifuged at 13000 r/min for 10 min. The supernatant was obtained, and 20 μl of the supernatant was injected for measurement. A standard curve was established using the plasma drug concentration ratio of the sample to the internal standard as abscissa and the peak area ratio of the sample to the internal standard as ordinate.

3.3 HPLC/MS conditions were the same as those in Experiment 1.

4. Results:

The main pharmacokinetic parameters and oral bioavailability results were calculated by using DAS2.0 (statistical moment).

| | Parameter | Unit | Mean | SD | RSD/% |
|---|---|---|---|---|---|
| tail intravenous injection | AUC(0-t) | μg/L * h | 12746.48 | 887.47 | 6.96 |
| | AUC(0-∞) | μg/L * h | 12983.81 | 990.41 | 7.63 |
| | t½z | h | 5.514 | 1.081 | 19.61 |
| | Tmax | h | 0.083 | 0 | 0 |
| | CLz | L/h/kg | 1.548 | 0.12 | 7.62 |
| | Vz | L/kg | 12.207 | 1.85 | 15.13 |
| | Cmax | μg/L | 3237.09 | 397.65 | 12.28 |
| intragastric gavage | AUC(0-t) | μg/L * h | 5244.93 | 1697.39 | 32.36 |
| | AUC(0-∞) | μg/L * h | 5552.57 | 2184.39 | 39.34 |
| | t½z | h | 5.564 | 2.42 | 43.57 |
| | Tmax | h | 6 | 2.45 | 40.82 |
| | CLz/F | L/h/kg | 3.989 | 1.26 | 31.46 |
| | Vz/F | L/kg | 30.07 | 12.11 | 40.29 |
| | Cmax | μg/L | 368.03 | 83.56 | 22.71 |

5. Conclusion

Method for the calculation of bioavailability:

$$F=(AUC_{ig} \times D_{iv})/(AUC_{iv} \times D_{ig}) \times 100\%$$

wherein D is dose; AUC: the area under the plasma drug concentration-time curve; ig represents intragastric administration; and iv represents intravenous injection administration.

N-[4-(3-chloro-4-fluorophenylamino)-7-(2-methoxyethoxy)quinazolin-6-yl]-2-[1-(2-methoxyethyl)piperidin-4-ylidene]acetamide dihydrobromide has a bioavailability of 42.76%, and has good pharmacokinetic properties.

Experiment III. Bioavailability Assay for N-[4-(3-chloro-4-fluorophenylamino)-7-(2-methoxyethoxy)quinazolin-6-yl]-2-[1-(2-methoxyethyl)piperidin-4-ylidene]acetamide 1. Experimental Animals:

8 Wistar rats (male, weighing 160-190 g) were purchased from Laboratory Animal Center, Chinese PLA Academy of Military Medical Sciences. License No.: SCXK (Army) 2012-0004; Certificate No.: 0037074.

2. Administration Scheme:

| Administration Route | Administration Dose | Drug Concentration | Administration Volume | Solvent | Number of Animals |
|---|---|---|---|---|---|
| tail intravenous injection (iv) | 20 mg/kg | 4 mg/ml | 5 ml/kg | pre-formulation | 4 |
| intragastric gavage (ig) | 20 mg/kg | 4 mg/ml | 5 ml/kg | | 4 |

Preparation of the Preformulation:

1) the compound was precisely weighed in a 10 ml glass tube;

2) The volume of DMSO was 2% of the total volume and DMSO was pipetted. The tip of the pipette was slowly rotated with being pressed against the inner wall of the centrifuge tube, and DMSO was pipetted in several times to dissolve the compound adsorbed on the wall of the centrifuge tube. After all the compound was transferred to the bottom portion of the centrifuge tube, the compound was dissolved by vortex and then placed in a water bath at 80° C.;

3) polyoxylethylene 35-castor oil of which the volume was 6% of the total volume was added and vortex;

4) sodium chloride solution for injection (0.9%) of which the volume was 92% of the total volume was added and vortexed to give a clear solution which will be used within 60 min Note: the total volume refers to the volume of the solution obtained upon completion of the preparation.

3. Assay Method:

3.1 Dosing regimens and Handling of Blood Samples:

8 rats were fasted and ad libitum accessed to water for 12 h before administration. They were randomly divided into two groups, i.e. four rats per group, and were administered with the drug according to the administration scheme. Blood (about 0.5 ml) was drawn from the orbital venous plexus before dosing and at 5 min, 0.5 h, 1 h, 2 h, 3 h, 4 h, 5 h, 6 h and 8 h after dosing, and put into a heparinized centrifuge tube and centrifuged at 8000 r/min for 10 min 100 µl of the plasma was recovered, and 200 µl of 0.2% acetic acid in methanol (containing an internal standard (irbesartan, 20 ng/ml)) was added thereto to precipitate protein, vortexed for 2 min and centrifuged at 13000 r/min for 10 min The supernatant was obtained, and 20 µl of the supernatant was injected for detection.

3.2 LC-MS detection Conditions:

(1) Chromatographic Conditions:

Chromatographic column: phenomenex Synergi Polar-RP (150×4.6 mm, 2.5 µm)

Flow rate: 1 ml/min; column temperature: 40° C.

Mobile phase: A phase: 5 mM aqueous solution of ammonium formate; B phase: methanol, and the gradient was as follows:

| Time (min) | A Phase | B Phase |
| --- | --- | --- |
| 0 | 60 | 40 |
| 3 | 15 | 85 |
| 4 | 15 | 85 |
| 4.5 | 60 | 40 |
| 8.5 | 60 | 40 |

(2) MS Conditions:

API3000 LC-MS/MS; ESI source; MRM positive ion scan mode; and the parameters were as follows:

| Compound | Ion Pair | CE (Collision Energy) |
| --- | --- | --- |
| compound 1 | 544.1→457.2 | 40 |
| internal standard (atorvastatin hemi-calcium salt) | 429.2→207.1 | 35 |

4. Results:

The main pharmacokinetic parameters and oral bioavailability results were calculated by using DAS2.0 (statistical moment).

| | Parameter | Unit | Mean | SD | RSD/% |
| --- | --- | --- | --- | --- | --- |
| tail intravenous injection | AUC(0-t) | µg/L * h | 11799 | 3418.6 | 29.0 |
| | AUC(0-∞) | µg/L * h | 13898 | 2790 | 20 |
| | t½z | h | 4.39 | 1.92 | 43.71 |
| | Tmax | h | 0.083 | 0 | 0 |
| | CLz | L/h/kg | 1.48 | 0.27 | 18.45 |
| | Vz | L/kg | 9.55 | 4.58 | 47.95 |
| | Cmax | µg/L | 13200 | 2956.3 | 22.4 |
| Intragastric gavage | AUC(0-t) | µg/L * h | 2186 | 170.84 | 7.81 |
| | AUC(0-∞) | µg/L * h | 3323 | 700.29 | 21.07 |
| | t½z | h | 4.59 | 1.51 | 32.87 |
| | Tmax | h | 2.5 | 0.577 | 23.08 |
| | CLz/F | L/h/kg | 6.20 | 1.17 | 18.93 |
| | Vz/F | L/kg | 39.23 | 4.58 | 11.68 |
| | Cmax | µg/L | 416.25 | 52.9 | 12.7 |

5. Conclusion

Method for the calculation of bioavailability:

$$F=(AUCig \times Div)/(AUCiv \times Dig) \times 100\%$$

wherein D is dose; AUC: the area under the plasma drug concentration-time curve; ig represents intragastric administration; and iv represents intravenous injection administration.

N-[4-(3-chloro-4-fluorophenylamino)-7-(2-methoxyethoxy)quinazolin-6-yl]-2-[1-(2-methoxyethyl)piperidin-4-ylidene]acetamide has a bioavailability of 23.9%, and has good pharmacokinetic properties.

Experiment IV Bioavailability Assay for N-[4-(3-chloro-4-fluorophenylamino)-7-(2-methoxyethoxy)quinazolin-6-yl]-2-[1-(2-methoxyethyl)piperidin-4-ylidene]acetamide Dimethylsulfonate in Rats 1. Experimental Animals:

12 SD rats (half of them were male and half of them were female, 7-10 weeks old, weighting 200-350 g) were purchased from Beijing Vital River Laboratory Animal Technology Co., Ltd., and reared in Animal House, GLP Center, Taiping Road No. 27 courtyard. Production License Number of Beijing Vital River Laboratory Animal Technology Co., Ltd. is SCXK (Beijing) 2009-0002.

2. Administration Scheme:

| Administration Route | Administration Dose | Drug Concentration | Administration Volume | Animal | Number of Animals |
| --- | --- | --- | --- | --- | --- |
| tail intravenous injection (iv) | 5 mg/kg | 0.5 mg/ml | 10 ml/kg | SD rat | 6 |
| intragastric gavage (ig) | 5 mg/kg | 0.5 mg/ml | 10 ml/kg | SD rat | 6 |

3. Assay Method:

3.1 Dosing Regimens and Handling of Blood Samples:

Blood (about 0.5 ml) was drawn with glass capillary from the orbital venous plexus at 1 mM, 5 mM, 15 mM, 30 mM, 1 h, 2 h, 3 h, 4 h, 6 h, 8 h, 12 h, and 24 h after dosing to each group of animals according to the administration scheme, and put into a heparinized centrifuge tube. The tube was gently shaken up and down, then centrifuged at 3000 r/min for 10 mM at 4° C. The plasma was separated. 50 μl of the plasma was pipetted into a centrifuge tube (5 ml), then 50% methanol aqueous solution (50 μl ) and thienorphine-D4 isotope (50 μl) as an internal standard were added thereto and vortexed. A solution of methanol:acetonitrile=1:3 (volume ratio) was added, vortexed for 30 s so as to mix thoroughly. The resulting mixture was centrifuged at 3000 r/min for 5 mM 500 μL of the supernatant was taken out, to which 500 μl of 20% methanol solution was added for serial dilution. The mixture was vortexed for 30 s so as to mix thoroughly. The mixture was centrifuged at 13000 r/min for 5 mM, and 104, of the supernatant was injected for LC/MS/MS assay.

3.2 LC-MS Detection Conditions:

Chromatographic column: Agela Venusil AQ-C18, 5 μm 2.1×50 mm; S/N: AQ-2105060029.

Liquid phase conditions: A: aqueous solution (5 mmol/L ammonium acetate, 0.2% formic acid), B: methanol; column temperature 25° C.; injection volume: 10 μL; gradient elution. Gradient conditions: A phase: 5 mM ammonium acetate (containing 0.2% formic acid); B phase: methanol; 0-0.5 min, A phase 0.21 mL/min, B phase 0.09 mL/min; 0.5-1 min, the flow rate of A phase was linearly reduced to 0 mL/min, the flow rate of B phase was linearly increased to 0.3 mL/min; 1.01 min, the flow rate of B phase was increased to 0.5 mL/min and maintained for 1 min; 2.01 min, the flow rate of A phase was increased to 0.21 mL/min, the flow rate of B phase was reduced to 0.09 mL/min, the ratio was maintained for 2 mM and equilibrated to initial flow rate ratio.

MS conditions: ion source: Turbo Ionspray (ESI+); detection mode: MRM; electrical parameters: compound 1: m/z 544.2-457.1, CE (collision energy): 36.5.

4. Results:

The main pharmacokinetic parameters and oral bioavailability results were calculated by using DAS2.0 (statistical moment).

The pharmacokinetic parameters of statistical moments (n=6) for a single intravenous injection of 5.0 mg/kg in rats

| Parameter | Unit | Parameter Value | |
| --- | --- | --- | --- |
| | | Mean | SD |
| AUC(0-t) | ng/ml · h | 1373.26 | 361.20 |
| AUC(0-∞) | ng/ml · h | 1458.34 | 322.74 |
| t½z | h | 4.06 | 0.50 |
| Tmax | h | 0.02 | 0.00 |
| CLz | L/h/kg | 2.63 | 0.52 |
| Vz | L/kg | 15.17 | 2.15 |
| Cmax | ng/ml | 1218.04 | 143.87 |

The pharmacokinetic parameters of statistical moments (n=6) for a single intragastric administration of 5.0 mg/kg in rats

| Parameter | Unit | Parameter Value | |
| --- | --- | --- | --- |
| | | Mean | SD |
| AUC(0-t) | ng/ml · h | 781.63 | 357.42 |
| AUC(0-∞) | ng/ml · h | 902.33 | 311.31 |
| t½z | h | 5.83 | 3.44 |
| Tmax | h | 3.33 | 2.58 |
| CLz/F | L/h/kg | 4.55 | 1.62 |
| Vz/F | L/kg | 36.92 | 22.29 |

| Parameter | Unit | Parameter Value | |
| --- | --- | --- | --- |
| | | Mean | SD |
| Cmax | ng/ml | 75.21 | 23.27 |
| F (%) | | 57 | |

5. Conclusion

Method for the calculation of bioavailability:

$$F=(AUC_{ig} \times D_{iv})/(AUC_{iv} \times D_{ig}) \times 100\%$$

wherein D is dose; AUC: the area under the plasma drug concentration-time curve; ig represents intragastric administration; and iv represents intravenous injection administration.

N-[4-(3-chloro-4-fluorophenylamino)-7-(2-methoxyethoxy)quinazolin-6yl]-2-[1-(2-methoxyethyl)piperidin-4-ylidene]acetamide dimethylsulfonate has a bioavailability of 56.9%, and has good pharmacokinetic properties.

Biological Example 2

MTD Assay for a Single Intragastric Gavage to Mice

1. Experimental Animals: ICR male mice, weighing 19-22 g, were purchased from Beijing Vital River Laboratory Animal Technology Co., Ltd., Animal License No. SCXK (Beijing) 2007-0001

2. Experimental Scheme: 21 mice were divided into nine groups: groups I, IV and VI referred to one mouse per group, groups II, V and IIX referred to four mice per group, and group III, VI and IX referred to two mice per group. Compound 4, compound 2 and compound 12 were dissolved in water for injection. Groups I-III were subjected to tail intravenous administration of compound 4 (N-[4-(3-chloro-4-fluorophenylamino)-7-(2-methoxyethoxy)quinazolin-6yl]-2-[piperidin-4-ylidene]acetamide dihydrochloride) at doses of 100 mg/kg, 150 mg/kg, and 200 mg/kg, respectively. The animal response and the weight change were observed after administration, and these animals were sacrificed after 14 days for anatomical observation. Groups IV-VI were subjected to tail intravenous administration of compound 2 (N-[4-(3-chloro-4-fluorophenylamino)-7-(2-methoxyethoxy)quinazolin-6yl]-2-[1-(2-methoxyethyl)piperidin-4-ylidene]acetamide dihydrochloride) at doses of 100 mg/kg, 150 mg/kg, and 200 mg/kg, respectively. The animal response and the weight change were observed after administration, and these animals were sacrificed after 14 days for anatomical observation. Groups VII-IX were subjected to tail intravenous administration of compound 12 (N-[4-(3-ethynylphenylamino-7-(2-ethoxy)quinazolin-6yl]-2-[1-methylpiperidin-4-ylidene]acetamide dihydrochloride) at doses of 100 mg/kg, 150 mg/kg, and 200 mg/kg, respectively. The animal response and the weight change were observed after administration, and these animals were sacrificed after 14 days for anatomical observation.

3. Experimental Results:
Compound 4: Death Situation and Anatomical Phenomenon of Mice

| Administration Dose (mg/kg) | Administration Volume (ml/kg) | Number of Experimental Animals | Number of Deaths | Mortality (%) | Anatomical Phenomenon |
|---|---|---|---|---|---|
| 100 | 10 | 1 | 0 | 0 | no significant abnormality was found after sacrifice and anatomy |
| 150 | 15 | 4 | 0 | 0 | no significant abnormality was found after sacrifice and anatomy |
| 200 | 20 | 2 | 1 | 50 | tumbling reflex of one of the animals disappeared after administration, and it died after 3 min, no significant abnormality was found after anatomy |

Compound 2: Death Situation and Anatomical Phenomenon of Mice

| Administration Dose (mg/kg) | Administration Volume (ml/kg) | Number of Experimental Animals | Number of Deaths | Mortality (%) | Anatomical Phenomenon |
|---|---|---|---|---|---|
| 100 | 10 | 1 | 0 | 0 | no significant abnormality was found after sacrifice and anatomy |
| 150 | 15 | 4 | 0 | 0 | no significant abnormality was found after sacrifice and anatomy |
| 200 | 20 | 2 | 0 | 0 | no significant abnormality was found after sacrifice and anatomy |

Compound 12: Death Situation and Anatomical Phenomenon of Mice

| Administration Dose (mg/kg) | Administration Volume (ml/kg) | Number of Experimental Animals | Number of Deaths | Mortality (%) | Anatomical Phenomenon |
|---|---|---|---|---|---|
| 100 | 10 | 1 | 0 | 0 | no significant abnormality was found after sacrifice and anatomy |
| 150 | 15 | 4 | 2 | 50 | no significant abnormality was found after sacrifice and anatomy |
| 200 | 20 | 2 | 2 | 100 | no significant abnormality was found after sacrifice and anatomy |

It was found from preliminary pharmacokinetic studies that compound 4 and compound 12 gathered in the gastrointestinal tract, and their oral bioavailability was very low.

N-[4-(3-chloro-4-fluorophenylamino)-7-(2-methoxyethoxy)quinazolin-6-yl]-2--[1((2-methoxyethyl))piperidin-4-ylidene]acetamide dihydrochloride is better tolerated and less toxic, and is thus more preferred clinical medication option.

Biological Example 3

Inhibitory Effect on Tyrosine Kinase Activity of EGFR

1. Reagents and Materials

EGFR: Invitrogen Company, Catalogue No. PV3872 pGT (poly(glutamic acid-tyrosine)): Sigma-Aldrich Company, Catalogue No. P0275 pY-20 (mouse anti-phosphotyrosine antibody-HRP (horseradish peroxidase)): Invitrogen Company, Catalogue No. 03-7720

TMB (3,3',5,5'-tetramethylbenzidine, HRP substrate): eBioscience Company, Catalogue No. 00-4201-56

96-well microtiter plate: Nunc Company, Catalogue No. 442404

2. Instruments and Equipments

Microplate Reader: Bio-Rad Company, Model 680

96-well microplate washer: Bio-Rad Company, Model 1575

3. Assay Method 3.1 General Method

Assay method refers to the reference "J. Moyer, E. Barbacci, K. Iwata, et al., Induction of apoptosis and cell cycle arrest by CP-358,774, an inhibitor of epidermal growth factor receptor tyrosine kinase Cancer Research 1997, 57: 4838-4848.", on the basis of which modification was made. The assay method is briefly described as follows:

3.1.1 At 4° C., 96-well microtiter plate was coated with 0.2 mg/mL pGT (as the substrate of enzyme) dissolved in PBS (phosphate buffer) overnight. Unbound pGT was washed away with a washing solution (0.05% Tween −20 in PBS), and the plate was dried in the air at room temperature for 2 h.

3.1.2 The enzyme reaction was performed in 50 µl reaction system containing 50 mM HEPEs (N-(2-hydroxyethyl) piperazine-N'-2-ethanesulfonic acid), pH 7.5, 0.01% BRIJ-35 (polyoxyethylene lauryl ether), 10 mM $MgCl_2$, 1 mM EGTA (ethylene glycol bis(2-aminoethyl ether)tetraacetic acid), with certain concentrations of ATP (adenosine triphosphate) and kinase, and proceeded for 30 min at room temperature. The phosphate group at the terminal of ATP can be transferred to tyrosine residues of pGT by kinase catalysis so as to phosphorylate the tyrosine residues.

3.1.3 A final concentration of 1% SDS (sodium dodecyl sulfate) was added to terminate the reaction. The phosphorylated tyrosine residues were identified using pY-20. HRP at the end of the antibody enabled TMB to take on color. Then equal amount of 2 N $H_2SO_4$ was added to terminate the reaction. OD value, which is positively correlated with the phosphorylation degree of tyrosine residues of pGT, was measured at 450 nm 3.2 The concentrations of the kinase and substrate ATP were determined with reference to the literature "Optimization of a LanthaScreen Kinase assay for EGFR (ErbB1)" (https://tools.lifetechnologies.com/content/sfs/manuals/EGFR_LanthaScreen_actity_Europium.pdf), published by Invitrogen Corporation. The selection criteria for the final concentrations are that the concentration of kinase enabling the yield of the product within the linear range of the detection system and the concentration of ATP approching Km (Michaelis constant) value.

3.3 Assay for determining the Activity of Compounds 3.3.1 An appropriate amount of a compound was dissolved in DMSO (dimethylsulfoxide) to prepare 2 mM stock solution. Then the stock solution was diluted with DMSO to obtain a working solution with a 50-fold concentration of the highest test concentration, and subjected to a 4-fold gradient dilution to obtain seven concentrations in total.

3.3.2 1 µl 50-fold concentration of the compound working solution was added into 44 µl reaction system (50 mM HEPEs, pH 7.5, 0.01% BRIJ-35, 10 mM $MgCl_2$, 1 mM EGTA, containing 44.4 ng/ml EGFR with 40 ng/ml final concentration), and vortexed. 5 µl 10-fold concentration of ATP dissolved in $H_2O$ (the concentration of ATP in EGFR assay is 100 µM, and in Her2 assay is 400 µM) was added to initiate the enzyme reaction followed by reaction at room temperature for 30 min 3.3.3 A positive solvent control group (PC) without the test compound and a negative solvent control group (NC) without ATP and the compound were simultaneously set up Inhibition rate of the compound was obtained by comparing the OD value of the administered group with that of the solvent control group, which was calculated as follows: inhibition rate=[1−(experiment value−NC mean value)/(PC mean value−NC mean value)]33 100%. The mean value of inhibition rate and SD (standard deviation) were determined by duplicate wells. A curve with the concentration of the compound as abscissa and being in logarithmic distribution and the mean value of inhibition rate as ordinate was plotted and fitted using four-parameter logistic function. The concentration of the compound at the curve point corresponding to 50% inhibition rate is $IC_{50}$ value.

Conditions for EGFR Assay

| Kinase | Kinase concentration (ng/ml) | ATP concentration (µM) | Reaction time (min) |
| --- | --- | --- | --- |
| EGFR | 40 | 10 | 30 |

4. Assay Results

Inhibitory Activity on EGFR ($IC_{50}$: nM)

| Compound | Assay Result |
| --- | --- |
| compound 1 | 0.4 |
| compound 2 | 0.5 |
| compound 3 | 0.4 |
| compound 5 | 0.3 |
| compound 6 | 0.6 |
| compound 7 | 0.5 |
| compound 8 | 0.8 |
| compound 9 | 0.5 |
| compound 10 | 0.3 |
| compound 11 | 0.4 |

Biological Example 4

Inhibitory Action on Tyrosine Kinase Activity of Mutant EGFR (L858R, L858R/T790M)

1. Main Reagents and Materials

EGFR(L858R): Invitrogen Corporation, catalogue No. PR7447A

EGFR(L858R/T790M): Invitrogen Corporation, catalogue No. PR8911A

P22(polypeptide substrate): GL Biochem Ltd., catalogue No. 112393

96-well plate: Corning Inc., catalogue No.3365

384-well plate: Corning Inc., catalogue No.3573

2. Main Instrument and Equipment

Caliper workstation

3. Assay Method 3.1 General Conditions for the Assay

| Kinase | Kinase Concentration (nM) | ATP Concentration (μM) | Polypeptide Concentration (μM) | Reaction Time (min) |
|---|---|---|---|---|
| EGFR (L858R) | 9 | 111 | 3 | 60 |
| EGFR (L858R/T790M) | 10 | 19 | 3 | 60 |

3.2 Formulation of Kinase Buffer: 50 mM HEPES, pH 7.5, 0.0015% Brij-35, 10 mM $MgCl_2$, and 2 mM DTT (dithiothreitol).

3.3 Formulation of Termination Solution: 100 mM HEPES, pH 7.5, 0.015% Brij-35, 0.2% Coating Reagent #3 (prepared by Caliper workstation), and 50 mM EDTA (ethylene diamine tetraacetic acid).

3.4 Dilution of the Compounds:

3.4.1 Formulation of a 50-fold concentration of a compound: for example, if the final concentration of the compound for assay is 12.5 nM, 50-fold concentration is 625 nM. The 50-fold concentration of the compound working solution was subjected to a 4-fold dilution with DMSO in a 96-well plate to obtain seven diluted concentrations in total.

3.4.2 Transferring the 5-fold concentration of compound to a reaction plate: 10 μl solution was transferred from each well of the above-mentioned 96-well plate to another 96-well plate, and then 90 μl kinase buffer was added. 5 μl solution was transferred from the above 96-well plate to a 384-well reaction plate. As a result, 5 μl 5-fold concentration of the compound dissolved in 10% DMSO is in the 384-well reaction plate. 5 μl 250 mM EDTA was added into the negative control wells.

3.5 Kinase Reaction 3.5.1 2.5-fold concentration of enzyme solution was formulated by the kinase using a kinase buffer.

3.5.2 2.5-fold concentration of substrate solution was formulated by the polypeptide and ATP using a kinase buffer.

3.5.3 10 μl 2.5-fold concentration of enzyme solution was added into the 384-well plate and incubated at room temperature for 10 min 3.5.4 10 μl 2.5-fold concentration of substrate solution was added into the 384-well plate and incubated at 28° C. for 1 h.

3.5.5 25 μl termination solution was added to terminate the reaction.

3.6 The substrate conversion rate data was read with Caliper.

3.7 Calculation of inhibition rate: the conversion rate was converted into inhibition rate.

Inhibition rate %=(max-conversion rate)/(max-min) ×100%, wherein max refers to the conversion rate of the DMSO control, min refers to the conversion of enzyme-free control. $IC_{50}$ values were determined by the inhibition curve.

Inhibitory Activity on Mutant EGFR ($IC_{50}$: nM)

| | EGFR (L858R) | EGFR (L858R/T790M) |
|---|---|---|
| compound 1 | 0.40 | 266 |
| compound 3 | 0.45 | 235 |

N-[4-(3-chloro-4-fluorophenylamino)-7-(2-methoxyethoxy)quinazolin-6yl]-2-[1-(2-methoxyethyl)piperidin-4-ylidene]acetamide and pharmaceutically acceptable salts thereof are highly selective and irreversible tyrosine kinase inhibitor, especially showing high inhibitory activity on EGFR, and thus are more preferable options for clinical medication.

Biological Example 5

In Vitro Inhibitory Action on Human Tumor Cells

1. Tested Cells and Main Reagents

Human epidermoid carcinoma cell line A431, human non-small cell lung cancer cell line HCC827, head and neck cancer cell lines Fadu and human pancreatic cancer cell line AsPC-1 were purchased from Cell Bank, Chinese Academy of Sciences.

RPMI-1640 (a kind of medium), Gibco Inc., Catalogue No. 31800-022, is a dry powder. A liquid medium was formulated in accordance with the instructions, and 2 g/L $NaHCO_3$ and 5.958 g/L HEPEs were added thereto in order to meet the requirement of cell culture.

EMEM (Minimum Essential Medium with Earle's salts), Gibco Inc., Catalogue No. 41500-034, is a dry powder. A liquid medium was formulated in accordance with the instructions, and 2.2 g/L $NaHCO_3$ and 5.958 g/L HEPEs were added thereto in order to meet the requirement of cell culture.

DMEM (Dulbecco's Modified Eagle's Medium), Gibco Inc., Catalogue No. 12800-017, is a dry powder. A liquid medium was formulated in accordance with the instructions, and 2.2 g/L $NaHCO_3$ and 5.958 g/L HEPEs were added thereto in order to meet the requirement of cell culture.

F-12K (Nutrient Mixture F12 Ham Kaighn's Modification), Sigma-Aldrich Inc., Catalogue No. N3520, is a dry powder. A liquid medium was formulated in accordance with the instructions, and 1.5 g/L $NaHCO_3$ and 2.383 g/L HEPEs were added thereto in order to meet the requirement of cell culture.

F-12 (Ham's F-12 Nutrient Mixture), Gibco Inc., Catalogue No. 21700-075, is a dry powder. A liquid medium was formulated in accordance with the instructions, and 1.76 g/L $NaHCO_3$ and 2.383 g/L HEPEs were added thereto in order to meet the requirement of cell culture.

FBS (fatal bovine serun), Hyclone Laboratories, Inc., Catalogue No. SV30087.

MTT (tetrazolium salt), Sigma Corporation, Catalogue No. M5655. 5 mg/ml stock solution was prepared using a phosphate buffer.

SRB (sulforhodamine): Sigma-Aldrich Inc., Catalogue No.S9012. 0.4% (w/v) working solution was prepared using 1% acetic acid.

2. Main Instruments and Equipments $CO_2$ cell incubator (Type 311 and 371), Thermo Fisher Scientific Inc.

Laminar flow hood (Type DL-CJ-2N), Beijing Donglian Har Instrument Manufacture Co. Ltd.

ELIASA (Type 680), Bio-Rad Laboratories, Inc.

96-well plate washer (Type 1575), Bio-Rad Laboratories, Inc.

3. Assay Method 3.1 Cell culture medium formulation (complete medium) generally follows those provided by Cell Bank, Chinese Academy of Sciences and ATCC (American Type Culture Collection), and the additives were adjusted in view of basal medium formulation.

3.2 Cell culture method: cells were cultured in the complete medium at 37° C. under 5% $CO_2$ and saturated humidity until logarithmic growth phase, i.e., adherent cells substantially approach complete confluence, and then collected for subsequent assay. For the adherent cells, they were firstly digested with trypsin/EDTA to detach.

3.3 A certain number of cells were seeded into 96-well cell culture plates (hereinafter referred to as 96-well plates). Various concentrations of compounds were added and co-cultured for a period of time (usually 3 days). Finally, total cellular protein in the wells was determined using SRB assay, or cell viability was determined with MTT assay.

3.3.1 The cell seeding concentration was determined by cell growth curve assay which completely simulates compound inhibition assay process. Different concentrations of cells were seeded into 96-well plates, and the suitable concentrations should be or approach the maximal seeding concentration maintaining the cells in logarithmic growth phase over the time span of the assay in the absence of the interference of the compounds.

3.3.2 Determination of total cellular protein using SRB assay: medium in the wells was recovered; 10% trichloroacetic acid was added to fix cells for more than 1 h and then removed; the cells were washed with $H_2O$, and then stained with 0.4% SRB for 15-30 min; excess SRB was removed, and the cells were washed with 1% acetic acid; 100 μl of 10 mM Tris(tris(hydroxymethyl)aminomethane) aqueous solution was added to dissolve the SRB bound with protein; and the detection was carried out at 570 nm wavelength.

3.3.3 Determination of cell viability using MTT assay: medium in the wells was recovered, and 100 μl basal medium (generally refers to a medium free of fetal bovine serum (FBS) and other additives) containing 0.5 mg/ml MTT was added to each well; the cells were then cultured for 3 h; the basal medium containing MTT was recovered, and 100 μl DMSO was added to each well to dissolve formazan; and the measurement was carried out at 490 nm wavelength.

3.3.4 Selection of SRB or MTT assay: MTT assay was used in the experiments of human epidermoid carcinoma cell line A431, head and neck cancer cell line Fadu and human pancreatic cancer cell line AsPC-1; and SRB assay was used in the experiment of human non-small cell lung cancer cell line HCC827.

3.4 Dilution and addition of compounds: the concentration of DMSO that can be tolerant by the cells was determined by DMSO tolerance assay, and thereby selecting the dilution and addition methods of compounds. The effects of different concentrations of DMSO on cell growth were determined by DMSO tolerance assay. Tolerance is defined as that the effect on the cell growth does not exceed 20%. Two methods are finally determined as follows.

Method I: 1-2 mg of a test compound was weighed and dissolved in DMSO to form 2 mM stock solution. The stock solution was diluted to 20 μM (or adjusted according to the needs of the assay) with the basal medium and subjected to a 3-fold gradient dilution (the DMSO concentration was maintained constant at 1% during the dilution) to obtain eight concentration groups; To assay wells were added 80 μl complete medium and 20 μl 10-fold concentration of compound working solution, and the final volume per well was 200 μl and DMSO concentration was 0.1%. The cell line involved was HCC827.

Method II: 1-2 mg of a test compound was weighed and dissolved in DMSO to form 2 mM stock solution. The initial concentration was adjusted according to the needs of the assay, and subjected to a 3-fold gradient dilution with DMSO to obtain a solution of the compound with eight concentrations in total; 99 μl complete medium and 1 μl the solution of the compound were added to each assay well, and the final volume per well was 200 μl and DMSO concentration was 0.5%. The cell lines involved were A431, Fadu, and AsPC-1.

3.5 Calculation of inhibitory activity of compounds: the assay includes a compound assay group, a positive solvent control group (PC) without a compound and a negative solvent control group (NC) without cells and a compound Inhibition rate=[1-(experiment value−NC mean value)/(PC mean value−NC mean value)]×100%. The mean value of inhibition rate and SD were determined by duplicate assay wells. A curve with the concentration of the compound as abscissa and being in logarithmic distribution, and the mean value of inhibition rate as ordinate, was plotted and fitted using a four-parameter logistic function. The concentration of the compound on the curve point corresponding to 50% inhibition rate is $IC_{50}$ value.

Culture Medium Formulation of Human Tumor Cell Lines and Cell Seeding Concentration

| Cell Line Name | Culture Medium Formulation | | | Cell Seeding Concentration (number/well) |
|---|---|---|---|---|
| | Basal Medium | Other Additives in addition to Serum | Complete Medium | |
| A431 | DMEM, F-12 | — | 45% DMEM, 45% F-12, 10% FBS | $7 \times 10^3$ |
| HCC827 | RPMI-1640 | 1 mM S.P (1 mmol sodium pyruvate solution); 2.5 g/L Glucose (2.5 g/L glucose solution) | 90% RPMI-1640, 10% FBS, 1 mM sodium pyruvate, 4.5 g/L Glucose | $2.5 \times 10^3$ |

-continued

| Cell Line Name | Culture Medium Formulation | | | Cell Seeding Concentration (number/well) |
|---|---|---|---|---|
| | Basal Medium | Other Additives in addition to Serum | Complete Medium | |
| Fadu | EMEM | 1 mM S.P (1 mmol sodium pyruvate solution) | 90% EMEM, 10% FBS, 1 mM sodium pyruvate | 5-7 × $10^3$ |
| AsPC-1 | 90% RPMI-1640 | 1 mM S.P (1 mmol sodium pyruvate solution); 2.5 g/L Glucose (2.5 g/L glucose solution) | 90% RPMI-1640, 10% FBS, 1 mM sodium pyruvate, 4.5 g/L Glucose | 8 × $10^3$ |

Note:
"—" indicates none.

4. Assay Results 4.1 Inhibitory Action on Human Epidermoid Carcinoma Cell Line A431

Inhibitory activity on human epidermoid cancer cell line A431 ($IC_{50}$: μM)

| Compound | Assay Result |
|---|---|
| compound 1 | 0.125 |
| compound 3 | 0.138 |

4.2 Inhibitory Activity on Human Non-small Cell Lung Cancer Cell Line HCC827

Inhibitory activity on human non-small cell lung cancer cell line HCC827 ($IC_{50}$: μM)

| Compound | Assay Result |
|---|---|
| compound 1 | 0.008 |
| compound 3 | 0.010 |

4.3 Inhibitory Activity on Human Head and Neck Cancer Cell Lines Fadu

Inhibitory activity on human head and neck cancer cell lines Fadu ($IC_{50}$: μM)

| Compound | Assay Result |
|---|---|
| compound 3 | 0.132 |

4.4 Inhibitory Activity on Human Pancreatic Cancer Cell Line AsPC-1

Inhibitory activity on human pancreatic cancer cell line AsPC-1($IC_{50}$: μM)

| Compound | Assay Result |
|---|---|
| compound 3 | 4.3 |

N-[4-((3-chloro-4-fluorophenylamino))-7-((2-methoxyethoxy))quinazolin-6-yl]-2-[1-((2-methoxyethyl))piperidin-4-ylidene]acetamide and pharmaceutically acceptable salts thereof are highly selective and irreversible tyrosine kinase inhibitor, especially showing high inhibitory activity on EGFR.

Biological Example 6

Evaluation on Pharmacodynamic Activity of A431 Human Epidermal Carcinoma Xenograft Model 1. Assay Method
Cell Culture:
Tumor cells were cultured in an incubator at 37° C. with 5% $CO_2$ using MEM medium containing 10% inactivated fetal calf serum, 100 U/ml penicillin and 100 82 g/ml streptomycin. The tumor cells in logarithmic growth phase were collected, adjusted to an appropriate density and injected subcutaneously into nude mice (0.2 ml per mouse). An xenograft model was established after a tumor was formed in the nude mice and passaged in vivo for more than three generations.

Inoculation and Grouping of Tumor:
The above-mentioned tumor-bearing mice were sacrificed by cervical dislocation. The tumor was taken out and cut into small tumor pieces (about 2 mm×2 mm×2 mm) under sterile conditions. The small tumor pieces were inoculated subcutaneously into nude mice with a trocar. When tumor in tumor-bearing nude mice grew to about 150±50 $mm^3$ in volume, the experimental animals were randomly divided into the following five groups with eight animals each: solvent control group, 20, 40 and 80 mg/kg dose groups of N-[4-(3-chloro-4-fluorophenylamino)-7-(2-methoxyethoxy) quinazolin-6-yl]-2-[1-(2-methoxyethyl)piperidin-4-ylidene] acetamide dimethylsulfonate, and a 50 mg/kg dose group of positive control drug tarceva. The animals in each group were subjected to intragastric administration once a day for 14 consecutive days. The day of grouping is assigned as day 0.

2. Assay End Point and Data Processing
Tumor volume is calculated as: volume =0.5×long diameter×short $diameter^2$. The relative tumor volume (RTV) was calculated based on the measurements as: RTV=$V_t/V_0$, wherein $V_0$ is the tumor volume measured when the animals were grouped to be administered (i.e., d0), and $V_t$ is the tumor volume when each measurement was taken. Relative tumor proliferation rate T/C was calculated based on relative tumor volume, in which T is the mean value of the relative tumor volume of the treatment group, and C is the mean value of the relative tumor volume of the solvent control group. T/C was calculated as follows: T/C=$T_{RTV}/C_{RTV}$× 100% ($T_{RTV}$: RTV of the treatment group; $C_{RTV}$: RTV of the solvent control group) Inhibition rate (%)= (mean tumor weight of the solvent control group−mean tumor weight of the treatment group)/mean tumor weight of the solvent control group×100%. Percentage of body weight change=$W_n/W_0 \times 100\%$ ($W_n$: mean body weight of experimental animals in each group at day n, $W_0$: mean body weight of experimental animals in each group at day 0).

3. Statistical Analysis

One-Way ANOVA test was conducted in SPSS13.0, performing statistical analysis between groups.

4. Assay Results

Tumor volume, relative tumor volume and T/C of each group at the end of the assay

| Group | Tumor Volume (mm$^3$, $\bar{x}$ ± S.D.) | Relative Tumor Volume ($\bar{x}$ ± S.D.) | T/C (%) |
|---|---|---|---|
| solvent control group | 1075.5 ± 454.9 | 7.5 ± 2.2 | 100.0 |
| compound 3 20 mg/kg | 424.9 ± 434.0*** | 2.3 ± 1.5*** | 30.6 |
| compound 3 40 mg/kg | 418.9 ± 284.7*** | 2.8 ± 2.3*** | 37.7 |
| compound 3 80 mg/kg | 254.7 ± 228.2*** | 1.4 ± 0.9***# | 19.1 |
| Tarceva (50 mg/kg) | 498.9 ± 263.4** | 3.5 ± 1.8*** | 47.3 |

In the tumor volume parameter and relative tumor volume parameter, p < 0.01 and *p < 0.001 were compared with the solvent control group;

Tumor Weight and Tumor Inhibition Rate of Each Group

| Group | Tumor Weight (g, $\bar{x}$ ± S.D.) | Tumor Inhibitor Rate (%) |
|---|---|---|
| solvent control | 0.740 ± 0.287 | — |
| compound 3 20 mg/kg | 0.232 ± 0.312*** | 68.6 |
| compound 3 40 mg/kg | 0.199 ± 0.153*** | 73.2 |
| compound 3 80 mg/kg | 0.107 ± 0.126*** | 85.6 |
| Tarceva (50 mg/kg) | 0.281 ± 0.252*** | 62.0 |

"—" indicates none or no valid data;
***p < 0.001 was compared with the solvent control group 5. Conclusion of the Assay The three dose groups of Compound 3 were all able to inhibit tumor growth, T/C were 30.6%, 37.7% and 19.1%, respectively, showing a good dose-effect relationship. T/C of the positive control group was 47.3%.

Tumor inhibition rates of the three dose groups of Compound 3 on A431 human epidermoid carcinoma xenograft model were 68.6%, 73.2% and 85.6%, respectively, showing a good dose-effect relationship. Tumor inhibition rate of the positive control group was 62.0%.

Body weights of the experimental animals in the three dose groups of Compound 3 were not significantly reduced, and no significant abnormality was observed in the experimental animals, both of which indicated that each dose of N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate would not produce significant toxicity in the experimental animals. Administration dose of Tarceva was MTD.

N-[4-((3-chloro-4-fluorophenylamino))-7-((2-methoxyethoxy))quinazolin-6-yl]-2-[1((2-methoxyethyl))piperidin-4-ylidene]acetamide dimethylsulfonate has a good anti-tumor activity and a wider therapeutic window, and thus is a more preferable option for clinical medication.

Biological Example 7

Evaluation on Pharmacodynamic Activity of FaDu Human Head and Neck Cancer Xenograft Model 1. Assay Method Cell Culture:

Tumor cells were cultured in an incubator at 37° C. with 5% $CO_2$ using MEM medium containing 10% inactivated fetal calf serum, 100 U/ml penicillin and 100 µg/ml streptomycin. The tumor cells in logarithmic growth phase were collected, adjusted to an appropriate density and injected subcutaneously into nude mice (0.2 ml per mouse). An xenograft model was established after tumor was formed in the nude mice and passaged in vivo for more than three generations.

Inoculation and Grouping of Tumor:

The above-mentioned tumor-bearing mice were sacrificed by cervical dislocation. The tumor was taken out and cut into small tumor pieces (about 2 mm×2 mm×2 mm) under sterile conditions. The small tumor pieces were inoculated subcutaneously into nude mice on the right shoulder blade with a trocar. When tumor in tumor-bearing nude mice grew to about 120±50 mm$^3$ in volume, the experimental animals were randomly divided into the following five groups with eight animals each: solvent control group, 20, 40 and 80 mg/kg dose groups of N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate, and a 50 mg/kg dose group of positive control drug tarceva. The animals in each group were subjected to intragastric administration daily for 14 consecutive days. The day of grouping is assigned as day 0.

2. Assay End Point and Data Processing

Tumor volume is calculated as: volume=0.5×long diameter×short diameter$^2$. The relative tumor volume (RTV) was calculated based on the measurements as: RTV=$V_t/V_0$, wherein $V_0$ is the tumor volume measured when the animals were grouped to be administered (i.e., d0), and $V_t$ is the tumor volume when each measurement was taken. Relative tumor proliferation rate T/C was calculated based on relative tumor volume, in which T is the mean value of the relative tumor volume of the treatment group, and C is the mean value of the relative tumor volume of the solvent control group. T/C was calculated as follows: T/C=$T_{RTV}/C_{RTV}$×100% ($T_{RTV}$: RTV of the treatment group; $C_{RTV}$: RTV of the solvent control group) Inhibition rate (%)=(mean tumor weight of the solvent control group−mean tumor weight of the treatment group)/mean tumor weight of the solvent control group×100%. Percentage of body weight change=$W_n/W_0$×100% ($W_n$: mean body weight of experimental animals in each group at day n, $W_0$: mean body weight of experimental animals in each group at day 0).

3. Statistical Analysis

One-Way ANOVA test was conducted in SPSS13.0, performing statistical analysis between groups.

4. Assay Results

Tumor volume, relative tumor volume and T/C of each group at the end of the assay

| Group | Tumor Volume (mm$^3$, $\bar{x}$ ± S.D.) | Relative Tumor Volume ($\bar{x}$ ± S.D.) | T/C (%) |
|---|---|---|---|
| solvent control | 1111.8 ± 318.2 | 10.0 ± 4.5 | 100.0 |
| compound 3 20 mg/kg | 703.3 ± 144.2** | 6.1 ± 1.3** | 61.4 |
| compound 3 40 mg/kg | 602.9 ± 204.4*** | 5.5 ± 1.9** | 54.7 |
| compound 3 80 mg/kg | 352.3 ± 157.0*** | 3.2 ± 1.6***## | 31.6 |
| Tarceva (50 mg/kg) | 709.9 ± 274.9 | 6.0 ± 1.4 | 59.9 | p < 0.01 and *p < 0.001 were compared with the solvent control group; and
p < 0.01 was compared with the positive control group.

Tumor Weight and Tumor Inhibition Rate of Each Group

| Group | Tumor Weight (g, x̄ ± S.D.) | Tumor Inhibitor Rate (%) |
|---|---|---|
| solvent control | 1.095 ± 0.366 | — |
| compound 3 20 mg/kg | 0.684 ± 0.192** | 37.5 |
| compound 3 40 mg/kg | 0.522 ± 0.427*** | 52.4 |
| compound 3 80 mg/kg | 0.260 ± 0.128***## | 76.2 |
| Tarceva (50 mg/kg) | 0.650 ± 0.267** | 40.6 |

"—" indicates none or no valid data;
$p < 0.01$ and *$p < 0.001$ were compared with the solvent control group; and
$p < 0.01$ was compared with the positive control group.

5. Conclusion of the Assay

T/C of each dose group of Compound 3 was 61.4%, 54.7% and 31.6%, respectively. Each dose group had good inhibitory activity on FaDu human head and neck cancer xenograft model.

Tumor inhibition rate of each dose group of Compound 3 was 37.5%, 52.4% and 76.2%, respectively. Each dose group of Compound 3 had good inhibitory activity on FaDu human head and neck cancer xenograft model.

Body weights of the experimental animals in each dose group of Compound 3 were not significantly reduced, and no significant abnormality was observed in the experimental animals, both of which indicated that each dose of Compound 3 would not produce significant toxicity in the experimental animals. Administration dose of Tarceva was MTD.

N-[4-((3-chloro-4-fluorophenylamino))-7-((2-methoxyethoxy))quinazolin-6-yl]-2-[1-((2-methoxyethyl))piperidin-4-ylidene]acetamide dimethylsulfonate has good anti-tumor activity and a wider therapeutic window, and thus is a more preferable option for clinical medication.

Biological Example 8

Evaluation on Pharmacodynamic Activity of HCC827 Human Non-Small Cell Lung Cancer Xenograft Model 1. Assay Method Cell Culture:

Tumor cells were cultured in an incubator at 37° C. with 5% $CO_2$ using MEM medium containing 10% inactivated fetal calf serum, 100 U/ml penicillin and 100 μg/ml streptomycin. The tumor cells in logarithmic growth phase were collected, adjusted to an appropriate density and injected subcutaneously into nude mice (0.2 ml per mouse). An xenograft model was established after a tumor was formed in the nude mice and passaged in vivo for more than three generations.

Inoculation and Grouping:

The above-mentioned tumor-bearing mice were sacrificed by cervical dislocation. The tumor was taken out and cut into small tumor pieces (about 2 mm×2 mm×2 mm) under sterile conditions. The small tumor pieces were inoculated subcutaneously into nude mice on the right shoulder blade with a trocar. When tumor in tumor-bearing nude mice grew to about 150±50 $mm^3$ in volume, the experimental animals were randomly divided into the following five groups with eight animals each: solvent control group, 20 mg/kg, 40 mg/kg and 80 mg/kg dose groups of N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate, and a 50 mg/kg dose group of positive control drug tarceva. The animals in each group were subjected to intragastric administration daily for 14 consecutive days. The day of grouping is assigned as day 0.

2. Assay End Point and Data Processing

Tumor volume is calculated as: volume=0.5×long diameter×short $diameter^2$. The relative tumor volume (RTV) was calculated based on the measurements as: $RTV=V_t/V_0$, wherein $V_0$ is the tumor volume measured when the animals were grouped to be administrated (i.e., d0), and $V_t$ is the tumor volume when each measurement was taken. Relative tumor proliferation rate T/C was calculated based on relative tumor volume, in which T is the mean value of the relative tumor volume of the treatment group, and C is the mean value of the relative tumor volume of the solvent control group. T/C was calculated as follows: $T/C=T_{RTV}/C_{RTV}×100\%$ ($T_{RTV}$: RTV of the treatment group; $C_{RTV}$: RTV of the solvent control group) Inhibition rate (%)=(mean tumor weight of the solvent control group−mean tumor weight of the treatment group)/mean tumor weight of the solvent control group x 100%. Percentage of body weight change=$W_n/W_0×100\%$ ($W_n$: mean body weight of experimental animals in each group at day n, $W_0$: mean body weight of experimental animals in each group at day 0).

3. Statistical Analysis

One-Way ANOVA test was conducted in SPSS13.0, performing statistical analysis between groups.

4. Assay Results

Tumor volume, relative tumor volume and T/C of each group at the end of the assay

| Group | Tumor Volume ($mm^3$, x̄ ± S.D.) | Relative Tumor Volume (x̄ ± S.D.) | T/C (%) |
|---|---|---|---|
| solvent control group | 1056.4 ± 259.3 | 7.16 ± 1.93 | 100.0 |
| compound 3 20 mg/kg | 57.3 ± 77.6*** | 0.36 ± 0.45*** | 5.0 |
| compound 3 40 mg/kg | 18.4 ± 11.6*** | 0.13 ± 0.10*** | 1.8 |
| compound 3 80 mg/kg | 20.9 ± 8.6*** | 0.13 ± 0.04*** | 1.8 |
| Tarceva (50 mg/kg) | 55.3 ± 46.3*** | 0.36 ± 0.27*** | 5.0 |

***$p < 0.001$ was compared with the solvent control group

Tumor Weight and Tumor Inhibition Rate of Each Group

| Group | Tumor Weight (g, x̄ ± S.D.) | Tumor Inhibitor Rate (%) |
|---|---|---|
| solvent control group | 0.545 ± 0.147 | — |
| compound 3 20 mg/kg | 0.045 ± 0.074*** | 91.7 |
| compound 3 40 mg/kg | 0.026 ± 0.026*** | 95.2 |
| compound 3 80 mg/kg | 0.014 ± 0.013*** | 97.4 |
| Tarceva (50 mg/kg) | 0.067 ± 0.055*** | 87.7 |

"—" indicates none or no valid data;
***$p < 0.001$ was compared with the solvent control group 5. Conclusion of the Assay T/C of the three dose groups of Compound 3 were 5.0%, 1.8% and 1.8%, respectively, showing a good dose-effect relationship. T/C of the positive control group was 5.0%.

Tumor inhibition rates of the three dose groups of Compound 3 were 91.7%, 95.2% and 97.4%, respectively.

Body weights of the experimental animals in each dose group of Compound 3 were not significantly reduced, and no significant abnormality was observed in the experimental animals, both of which indicated that each dose of Compound 3 would not produce significant toxicity in the experimental animals. Administration dose of Tarceva was MTD.

N-[4-((3-chloro-4-fluorophenylamino))-7-((2-methoxy-ethoxy))quinazolin-6-yl]-2-[1-((2-methoxyethyl))piperidin-4-ylidene]acetamide dimethylsulfonate has good anti-tumor activity and a wider therapeutic window, and thus is a more preferable option for clinical medication.

Biological Example 9

Mutagenicity Assay on *Salmonella Typhimurium*

1. Materials and Methods:
Compound 1: N-[4-(3-chloro-4-fluorophenylamino)-7-(2-methoxyethoxy)quinazolin-6-yl]-2-[1-(2-methoxyethyl)piperidin-4-ylidene]acetamide
Compound 3: N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate
Direct mutagen 1: Dexon (Dima Technology Inc.; Batch No.: 456-2D)
Direct mutagen 2: sodium azide, SA (Amresco Inc.; Batch No.: 0580c509)
Indirect mutagen: 2-aminoanthracene, 2-AA (Sigma-Aldrich Inc.; Batch No.: STBB1901V)
Strains: histidine auxotrophic mutants of *salmonella typhimurium* TA97, TA98, TA100, TA1535, and TA102 (Institute of Laboratory Animal Science, Chinese Academy of Medical Sciences) are cryopreserved in liquid nitrogen.
Vehicle 1: dimethyl sulfoxide, DMSO (Beijing Chemical Works; Batch No.: 20111209)
Vehicle 2: sterile water for injection (Tianjin Pharmaceutical Jiaozuo Co., Ltd.; Batch No.: 11080142)

2. Identification of the Genetic Characteristics of the Strains

The genetic characteristics of the strains had been identified and accredited, including spontaneous revertant rate test, histidine demanding test, crystal violet sensitivity test, identification test for excision repair deficient mutation of UV damage, ampicillin resistance test, and tetracycline resistance test.

3. Enrichment Culture of the Strains

Bacteria suspension cryopreserved in liquid nitrogen was quickly thawed in a 37° C. water bath. 100 µL bacteria suspension was withdrawn and seeded into 20 mL nutrient broth. After static culture in the dark at 37° C. for 16 h, the bacteria suspension was taken for mutagenicity assay.

4. Assay Method
4.1 Assay Group 4.2 Formulation of the Test Samples

Compound 1 was weighed and dissolved in DMSO at a final concentration of 15 mg/mL. The solution was filtered through a 0.22 µm filter membrane. 1.0 mL initial filtrate was discarded during filtrating. Then the filtrated test sample solution (15 mg/mL) was gradiently diluted with DMSO to solutions having the concentrations of 5, 1.5, 0.5 and 0.15 mg/mL.

Compound 3 was weighed and dissolved in sterile water for injection at a final concentration of 15 mg/mL. The solution was filtered through a 0.22 µm filter membrane, 1.0 mL initial filtrate was discarded during filtrating. Then the filtrated test sample solution (15 mg/mL) was gradiently diluted with sterile water for injection to solutions having the concentrations of 5, 1.5, 0.5 and 0.15 mg/mL.

4.3 Concentration Assay for the Test Samples 15 mg/mL test sample solution was kept in duplicate (0.5 mL in volume each) before filtration. After formulation and filtration, each concentration of the filtrated test sample solutions was kept in duplicate (0.5 mL in volume each) and stored at room temperature. Accuracy of the concentration was analyzed by HPLC method.

HPLC method: octadecyl silane chemically bonded to silica gel was used as filler (4.6 mm×250 mm, 5 µm); 0.3% acetic acid aqueous solution (v/v, pH was adjusted with aqueous ammonia to 8.10±0.05)—methanol-acetonitrile(1:7)=48:52(v/v) as mobile phase; flow rate was 1 ml per min; column temperature was 40° C.; detection wavelength was 254 nm; and running time was 30 min.

4.4 Storage and Disposal of the Formulated Test Sample Solution

The formulated test sample solutions were stored at room temperature before dosing. The remaining test sample solutions were disposed as medical waste after the end of dosing.

4.5 Formulation of the Positive Control

Dexon: an appropriate amount of Dexon was weighed and dissolved in sterile water for injection to obtain a solution with a concentration of 250 µg/mL. The solution was used after being filtered through 0.22 µm sterile filter membrane.

Sodium azide: an appropriate amount of sodium azide was weighed and dissolved in sterile water for injection to obtain a solution with a concentration of 60 µg/mL. The solution was used after being filtered through 0.22 µm sterile filter membrane.

| Group | Test Sample/ Control | Dose (µg/plate) | TA97 (n) -S9 | TA97 (n) +S9 | TA98 (n) -S9 | TA98 (n) +S9 | TA100 (n) -S9 | TA100 (n) +S9 | TA102 (n) -S9 | TA102 (n) +S9 | TA1535 (n) -S9 | TA1535 (n) +S9 |
|---|---|---|---|---|---|---|---|---|---|---|---|---|
| 1 | sterile water for injection | — | 3 | 3 | 3 | 3 | 3 | 3 | 3 | 3 | 3 | 3 |
| 2 | DMSO | — | 3 | 3 | 3 | 3 | 3 | 3 | 3 | 3 | 3 | 3 |
| 3 | compound 1 | 1500 | 3 | 3 | 3 | 3 | 3 | 3 | 3 | 3 | 3 | 3 |
| 4 | compound 1 | 500 | 3 | 3 | 3 | 3 | 3 | 3 | 3 | 3 | 3 | 3 |
| 5 | compound 1 | 150 | 3 | 3 | 3 | 3 | 3 | 3 | 3 | 3 | 3 | 3 |
| 6 | compound 1 | 50 | 3 | 3 | 3 | 3 | 3 | 3 | 3 | 3 | 3 | 3 |
| 7 | compound 1 | 15 | 3 | 3 | 3 | 3 | 3 | 3 | 3 | 3 | 3 | 3 |
| 8 | compound 3 | 1500 | 3 | 3 | 3 | 3 | 3 | 3 | 3 | 3 | 3 | 3 |
| 9 | compound 3 | 500 | 3 | 3 | 3 | 3 | 3 | 3 | 3 | 3 | 3 | 3 |
| 10 | compound 3 | 150 | 3 | 3 | 3 | 3 | 3 | 3 | 3 | 3 | 3 | 3 |
| 11 | compound 3 | 50 | 3 | 3 | 3 | 3 | 3 | 3 | 3 | 3 | 3 | 3 |
| 12 | compound 3 | 15 | 3 | 3 | 3 | 3 | 3 | 3 | 3 | 3 | 3 | 3 |
| 13 | 2-AA | 3 | 3 | 3 | 3 | 3 | 3 | 3 | 3 | 3 | 3 | 3 |
| 14 | Dexon | 25 | 3 | — | 3 | — | 3 | — | 3 | — | — | — |
| 15 | SA | 6 | — | — | — | — | — | — | — | — | 3 | — |

Note:
Groups 1 and 2 are vehicle control groups. Groups 3-12 are the test sample groups; Groups 13-15 are positive control groups; and "n" is the number of plates.

2-aminoanthracene: an appropriate amount of 2-aminoanthracene was weighed and dissolved in DMSO to obtain a solution with a concentration of 30 μg/mL. The solution was used after being filtered through 0.22 μm sterile filter membrane.

4.6 Preparation and Formulation of S9 Mixture

The Sprague-Dawley rat liver S9 fraction used in this assay was prepared on May 18, 2012 with Batch No.: 20120518. It was stored in liquid nitrogen and the protein concentration is 20.477 mg/mL, which can be used before May 17, 2014. Sterility test and biological activity detection met the requirements of the assay. S9 mixture was formulated under sterile conditions based on the composition ratios shown in the table below.

Before use, S9 mixture was formulated under sterile conditions. The formulated volume was determined by operator according to the requirements of the assay. Other solvents were formulated in accordance with the standard operating procedures of the Centre. The formulation of S9 mixture followed the table below.

| Component | Concentration in S9 mixture |
|---|---|
| S9 | 10% |
| 0.4 mol/L MgCl$_2$ | 8 mM |
| 1.65 mol/L KCl | 33 mM |
| glucose-6-phosphate sodium salt (molecular weight 282.1) | 5 mM |
| NADPNa$_2$ (molecular weight 787.4) | 4 mM |
| 0.2 mol/L PBS (pH 7.4) | 100 mM |

4.6 Assay Procedures

The top medium was heated to be melt, and then balanced in a 45° C. water bath for further use.

0.1 mL test article or control drug solution, 0.5 mL S9 mixture or PBS (pH7.4), and 2.0 mL top medium (containing about 0.05 mM histidine, about 0.05 mM biotin, about 0.6% agar, and about 0.5% NaCl) in sequence, and 0.1 mL bacteria culture solution finally were added into glass test tubes (10 mL). The mixture was rapidly mixed uniformly on a vortex mixer and poured into the surface of the bottom medium. The top medium was spread evenly over the surface of the basal medium by slight rotation.

The plates were placed on a horizontal table until the medium were solidified. Then the plates were inverted and cultured at 37° C. for 48 h (except for the TA102 strain, which was cultured for 72 h). The plates were withdrawn to count the number of visible revertant colonies per plate. The precipitation phenomenon of the test samples was observed when loading and at the end of culture. Three plates were tested for each group under activation and non-activation conditions, respectively.

5. Assessment of the Results

The results were represented as the number of revertant colonies per plate, and the mean number of revertant colonies of each group and standard deviation were calculated. If the results meet the following one or two criteria, it would be assessed as positive. The biological significance of the assay results was firstly considered and the results of statistical tests were referred when assessing the results 1) For at least one strain, the number of revertant mutation colonies shows dose-dependent increase under the conditions with or without metabolic activation.

2) The number of revertant mutation colonies in one or more dose groups shows a significant increase under the conditions with or without metabolic activation, which can be repeated. Determining whether the test articles have antibacterial toxicity in the strains according to the following criteria:

1) background bacterial lawn become thin, which may be simultaneously accompanied by a reduction in the number of revertant mutation colonies.

2) absence of background bacterial lawn, i.e., bacterial growth was completely inhibited.

3) appearance of needle-like non-revertant mutation small colonies (usually accompanied by the absence of background bacterial lawn).

6. Data Processing Method

Statistical analysis was performed using a two-tailed test, and statistical significance level was set at P≤0.05. Statistics were done on the mean value and standard deviation of the number of revertant mutation colonies.

Data were analyzed according to the following procedure: Levene's Test was firstly performed for data homogeneity test. Single-factor analysis of variance test (ANOVA) would be performed if the data were homogeneous (P>0.05); and Dunnett's multiple comparisons would be performed if analysis of variance was significant (P≤0.05). Kruskal-wallis nonparametric test would be performed if the result of Levene's Test was significant (P≤0.05). Pairwise comparisons would be further performed using Mann-Whitney U test if the result of Kruskal-wallis nonparametric test was significant (P≤0.05).

7. Results 7.1 Analysis Results of the Test Samples

Test on Compound 1: the analysis results show that the highest concentration before filtering and each concentration of the test sample solution after filtering were between 101.77% and 104.31% of the theoretical concentration. The filter membrane did not show significant effect on the concentration of the solution within the acceptable range of 90%-110%.

Test on Compound 3: the analysis results show that the accuracy of the highest concentration before filtering and each concentration of the test sample solution after filtering were between 99.39% and 102.89% of the theoretical concentration. The filter membrane did not show significant effect on the concentration of the solution within the acceptable range of 90%-110%.

7.2 Morphologic Observation on the Background Bacterial Lawn and Colonies

TA97 strain at a dose of 1500 μg/plate had antibacterial toxicity under metabolic activation (adding S9) conditions, which was shown as the appearance of needle-like small colonies on the background bacterial lawn and the significant reduction (P≤0.05) in the number of revertant mutation colonies;

TA102 strain at doses of 1500 μg/plate and 500 μg/plate had antibacterial activity under metabolic or non-metabolic activation (without adding S9) conditions, which was shown as the significant reduction (P≤0.05) in the number of revertant mutation colonies;

No significant antibacterial activity was found in the rest strains at each dose under metabolic or non-metabolic activation conditions.

7.3 Observation on Precipitation Phenomenon

Where each strain was at a dose within the range of 150-1500 μg/plate under non-metabolic activation conditions and at doses of 500 μg/plate and 1500 μg/plate under metabolic activation conditions, the system became white turbid after adding the test sample solution, and kept on after adding to the top layer at doses of 500 μg/plate and 1500 μg/plate. It indicated that precipitation occurred in the culture system at these doses, and no precipitation phenomenon occurred in the rest groups. No precipitation phenomenon occurred in each dose group at the end of the culture.

7.4 Colony Count

The assay results shows that, as to the vehicle control group under metabolic or non-metabolic activation conditions, the number of spontaneous revertant mutation colonies of each strain was within the normal range in our laboratory; as to the dexon and sodium azide positive control groups under non-metabolic activation conditions and 2-aminoanthracene positive control group under metabolic activation conditions, the numbers of revertant mutation colonies were significantly increased (P≤0.05) with obviously more than 2-fold or more of the number of revertant mutation colonies in the vehicle control group, showing the expected positive results.

TA102 strain at doses between 15 μg/plate and 150 μg/plate, TA97 strain at doses between 15 μg/plate and 500 μg/plate, and the rest strains at doses between 15 μg/plate and 1500 μg/plate had no increase in the number of revertant mutation colonies relating to the test sample. The slightly but statistically significant (P≤0.05) changes of each strain at doses within the corresponding range on the number of revertant mutation colonies were considered as normal fluctuations within normal range. The assay results indicated that the test articles at doses of less than and equal to 150 μg/plate, 500 μg/plate and 1500 μg/plate had no mutagenicity on TA102 strain, TA97 strain and the rest strains, correspondingly.

8. Conclusion

Under the assay conditions, Compound 1 and Compound 3 had no mutagenicity on TA102 strain at doses of less than and equal to 150 μg/plate; no mutagenicity on TA97 strain at doses of less than and equal to 500 μg/plate; and no mutagenicity on TA98, TA100 and TA1535 strains at doses of less than and equal to 1500 μg/plate. Compound 1 and Compound 3 had no mutagenicity on all of the strains at a dose having no antibacterial toxicity.

N-[4-((3-chloro-4-fluorophenylamino))-7-((2-methoxyethoxy))quinazolin-6-yl]-2-[1-((2-methoxyethyl))piperidin-4-ylidene]acetamide and N-[4-((3-chloro-4-fluorophenylamino))-7-((2-methoxyethoxy))quinazolin-6-yl]-2-[1-((2-methoxyethyl))piperidin-4-ylidene]acetamide dimethylsulfonate have no Ames toxicity, and are more preferable option for clinical medication.

In view of the above, it will be appreciated that, although specific embodiments of the present application have been described herein for purposes of illustration, various variations or improvements may be made by a person skilled in the art without deviating from the spirit and scope of the present application. These variations or modifications all should be fall into the scope of the appended claims of the present application.

What is claimed is:

1. N-[4-(3-chloro-4-fluorophenylamino)-7-(2-methoxyethoxy) quinazolin-6-yl]-2-[1-(2-methoxyethyl)piperidin-4-ylidene]acetamide or a pharmaceutically acceptable salt thereof.

2. N-[4-(3-chloro-4-fluorophenylamino)-7-(2-methoxyethoxy) quinazolin-6-yl]-2-[1(2-methoxyethyl)piperidin-4-ylidene]acetamide or a pharmaceutically acceptable salt thereof according to claim 1, wherein the acid used to form the salt is selected from the group consisting of hydrochloric acid, hydrobromic acid, sulfuric acid, nitric acid, phosphoric acid, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid and undecylenic acid.

3. N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof according to claim 1, wherein the salt is selected from the group consisting of:

N-[4-(3-chloro-4-fluorophenylamino)-7-(2-methoxyethoxy)quinazolin-6-yl]-2-[1-(2-methoxyethyl)piperidin-4-ylidene]acetamide dihydrochloride;

N-[4-(3-chloro-4-fluorophenylamino)-7-(2-methoxyethoxy)quinazolin-6-yl]-2-[1-(2-methoxyethyl)piperidin-4-yliene]acetamide disulfate;

N-[4-(3-chloro-4-fluorophenylamino)-7-(2-methoxyethoxy)quinazolin-6-yl]-2-[1-(2-methoxyethyl)piperidin-4-ylidene]acetamide dihydrobromide;

N-[4-(3-chloro-4-fluorophenylamino)-7-(2-methoxyethoxy)quinazolin-6-yl]-2-[1-(2-methoxyethyl)piperidin-4-ylidene]acetamide dinitrate;

N-[4-(3-chloro-4-fluorophenylamino)-7-(2-methoxyethoxy)quinazolin-6-yl]-2-[1-(2-methoxyethyl)piperidin-4-ylidene]acetamide diphosphate;

N-[4-(3-chloro-4-fluorophenylamino)-7-(2-methoxyethoxy)quinazolin-6-yl]-2-[1-(2-methoxyethyl)piperidin-4-ylidene]acetamide diacetate;

N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate;

N-[4-(3-chloro-4-fluorophenylamino)-7-(2-methoxyethoxy)quinazolin-6-yl]-2-[1-(2-methoxyethyl)piperidin-4-ylidene]acetamide diphenylsulfonate;

N-[4-(3-chloro-4-fluorophenylamino)-7-(2-methoxyethoxy)quinazolin-6-yl]-2-[1-(2-methoxyethyl)piperidin-4-ylidene]acetamide difumarate;

N-[4-(3-chloro-4-fluorophenylamino)-7-(2-methoxyethoxy)quinazolin-6-yl]-2-[1-(2-methoxyethyl)piperidin-4-ylidene]acetamide dimaleate;

N-[4-(3-chloro-4-fluorophenylamino)-7-(2-methoxyethoxy)quinazolin-6-yl]-2-[1-(2-methoxyethyl)piperidin-4-ylidene]acetamide dinicotinate;

N-[4-(3-chloro-4-fluorophenylamino)-7-(2-methoxyethoxy)quinazolin-6-yl]-2-[1-(2-methoxyethyl)piperidin-4-ylidene]acetamide dioleate;

N-[4-(3-chloro-4-fluorophenylamino)-7-(2-methoxyethoxy)quinazolin-6-yl]-2-[1-(2-methoxyethyl)piperidin-4-ylidene]acetamide dioxalate;

N-[4-(3-chloro-4-fluorophenylamino)-7-(2-methoxyethoxy)quinazolin-6-yl]-2-[1-(2-methoxyethyl)piperidin-4-ylidene]acetamide dipropionate;

N-[4-(3-chloro-4-fluorophenylamino)-7-(2-methoxyethoxy)quinazolin-6-yl]-2-[1-(2-methoxyethyl)piperidin-4-ylidene]acetamide disalicylate;

N-[4-(3-chloro-4-fluorophenylamino)-7-(2-methoxyethoxy)quinazolin-6-yl]-2-[1-(2-methoxyethyl)piperidin-4-ylidene]acetamide bis(4-aminosalicylate);

N-[4-(3-chloro-4-fluorophenylamino)-7-(2-methoxyethoxy)quinazolin-6-yl]-2-[1-(2-methoxyethyl)piperidin-4-ylidene]acetamide diacetyl salicylate;

N-[4-(3-chloro-4-fluorophenylamino)-7-(2-methoxyethoxy)quinazolin-6-yl]-2-[1-(2-methoxyethyl)piperidin-4-ylidene]acetamide ditartrate;

N-[4-(3-chloro-4-fluorophenylamino)-7-(2-methoxyethoxy)quinazolin-6-yl]-2-[1-(2-methoxyethyl)piperidin-4-ylidene]acetamide di(p-toluenesulfonate);

N-[4-(3-chloro-4-fluorophenylamino)-7-(2-methoxyethoxy)quinazolin-6-yl]-2-[1-(2-methoxyethyl)piperidin-4-ylidene]acetamide dicitrate;

N-[4-(3-chloro-4-fluorophenylamino)-7-(2-methoxyethoxy)quinazolin-6-yl]-2-[1-(2-methoxyethyl)piperidin-4-ylidene]acetamide dimalate;

N-[4-(3-chloro-4-fluorophenylamino)-7-(2-methoxyethoxy)quinazolin-6-yl]-2-[1-(2-methoxyethyl)piperidin-4-ylidene]acetamide bis(naphthalene-1,5-disulfonate);

N-[4-(3-chloro-4-fluorophenylamino)-7-(2-methoxyethoxy)quinazolin-6-yl]-2-[1-(2-methoxyethyl)piperidin-4-ylidene]acetamide bis(decanedioate); and N-[4-(3-chloro-4-fluorophenylamino)-7-(2-methoxyethoxy)quinazolin-6-yl]-2-[1-(2-methoxyethyl)piperidin-4-ylidene]acetamide bis(L-aspartate).

4. A pharmaceutical composition comprising N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof and a pharmaceutically acceptable carrier, diluent or excipient.

5. A method for treating a cancer, comprising administering to a subject in need thereof a therapeutically effective amount of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof according to claim 1, wherein the cancer is selected from the group consisting of: epidermoid carcinoma, breast cancer, head and neck cancer, non-small cell lung cancer, colon cancer, pancreatic cancer, esophagus cancer, stomach cancer and prostate cancer.

6. A method for treating a cancer in a subject, comprising administering to the subject a pharmaceutical composition comprising a therapeutically effective amount of N-[4-(3-chloro-4-fluorophenylamino)-7- (2-methoxyethoxy)quinazolin-6-yl]-2-[1-(2-methoxyethyl)piperidin-4-ylidene]acetamide or a pharmaceutically acceptable salt thereof, and a pharmaceutically acceptable carrier, diluent or excipient, wherein the cancer is selected from the group consisting of epidermoid carcinoma, breast cancer, head and neck cancer, non-small cell lung cancer, colon cancer, pancreatic cancer, esophagus cancer, stomach cancer and prostate cancer.

7. The method of claim 6, wherein the therapeutically effective amount is a unit dose of N-[4-(3-chloro-4-fluorophenylamino)- 7-(2-methoxyethoxy)quinazolin-6-yl]-2-[1-(2-methoxyethyl)piperidin-4-ylidene]acetamide or a pharmaceutically acceptable salt thereof as an effective ingredient of 0.1 mg-1000 mg.

8. The method of claim 5, wherein the subject is a mammal.

9. The method of claim 8, wherein the mammal is a human.

10. The method of claim 5, wherein the therapeutically effective amount is a unit dose of N-[4-(3-chloro-4-fluorophenylamino)-7-(2-methoxyethoxy)quinazolin-6-yl]-2-[1-(2-methoxyethyl)piperidin-4-ylidene]acetamide or a pharmaceutically acceptable salt thereof as an effective ingredient of 0.1 mg-1000 mg.

11. The method of claim 6, wherein the subject is a human.

12. The pharmaceutical composition of claim 4, wherein the acid used to form the salt is selected from the group consisting of hydrochloric acid, hydrobromic acid, sulfuric acid, nitric acid, phosphoric acid, acetic acid, 2,2-dichloroacetic acid, adipic acid, alginic acid, ascorbic acid, aspartic acid, methylsulfonic acid, benzenesulfonic acid, benzoic acid, 4-acetamidobenzoic acid, camphanic acid, camphor-10-sulfonic acid, capric acid, caproic acid, caprylic acid, carbonic acid, cinnamic acid, citric acid, cyclamic acid, dodecyl sulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleinic acid, orotic acid, oxalic acid, palmitic acid, pamoic acid, propionic acid, pyroglutamic acid, pyruvic acid, salicylic acid, 4-aminosalicylic acid, acetosalicylic acid, sebacic acid, stearic acid, succinic acid, tartaric acid, thiocyanic acid, p-toluenesulfonic acid, trifluoroacetic acid and undecylenic acid.

13. The pharmaceutical composition of claim 4, wherein the salt is selected from the group consisting of N-[4-(3-chloro-4-fluorophenylamino)-7-(2-methoxyethoxy)quinazolin-6-yl]-2-[1-(2-methoxyethyl)piperidin-4-ylidene]acetamide dihydrochloride;

N-[4-(3-chloro-4-fluorophenylamino)-7-(2-methoxyethoxy)quinazolin-6-yl]-2-[1-(2-methoxyethyl)piperidin-4-ylidene]acetamide disulfate;

N-[4-(3-chloro-4-fluorophenylamino)-7-(2-methoxyethoxy)quinazolin-6-yl]-2-[1-(2-methoxyethyl)piperidin-4-ylidene]acetamide dihydrobromide;

N-[4-(3-chloro-4-fluorophenylamino)-7-(2-methoxyethoxy)quinazolin-6-yl]-2-[1-(2-methoxyethyl)piperidin-4-ylidene]acetamide dinitrate;

N-[4-(3-chloro-4-fluorophenylamino)-7-(2-methoxyethoxy)quinazolin-6-yl]-2-[1-(2-methoxyethyl)piperidin-4-ylidene]acetamide diphosphate;

N-[4-(3-chloro-4-fluorophenylamino)-7-(2-methoxyethoxy)quinazolin-6-yl]-2-[1-(2-methoxyethyl)piperidin-4-ylidene]acetamide diacetate;

N-[4-(3-chloro-4-fluorophenylamino)-7-(2-methoxyethoxy)quinazolin-6-yl]-2-[1-(2-methoxyethyl)piperidin-4-ylidene]acetamide dimethylsulfonate;

N-[4-(3-chloro-4-fluorophenylamino)-7-(2-methoxyethoxy)quinazolin-6-yl]-2-[1-(2-methoxyethyl)piperidin-4-ylidene]acetamide diphenyl sulfonate;

N-[4-(3-chloro-4-fluorophenylamino)-7-(2-methoxyethoxy)quinazolin-6-yl]-2-[1-(2-methoxy ethyl)piperidin-4-ylidene]acetamide difumarate;

N-[4-(3-chloro-4-fluorophenylamino)-7-(2-methoxyethoxy)quinazolin-6-yl]-2-[1-(2-methoxyethyl)piperidin-4-ylidene]acetamide dimaleate;

N-[4-(3-chloro-4-fluorophenylamino)-7-(2-methoxyethoxy)quinazolin-6-yl]-2-[1-(2-methoxyethyl)piperidin-4-ylidene]acetamide dinicotinate;

N-[4-(3-chloro-4-fluorophenylamino)-7-(2-methoxyethoxy)quinazolin-6-yl]-2-[1-(2-methoxyethyl)piperidin-4-ylidene]acetamide dioleate;

N-[4-(3-chloro-4-fluorophenylamino)-7-(2-methoxyethoxy)quinazolin-6-yl]-2-[1-(2-methoxyethyl)piperidin-4-ylidene]acetamide dioxalate;

N-[4-(3-chloro-4-fluorophenylamino)-7-(2-methoxyethoxy)quinazolin-6-yl]-2-[1-(2-methoxyethyl)piperidin-4-ylidene]acetamide dipropionate;

N-[4-(3-chloro-4-fluorophenylamino)-7-(2-methoxyethoxy)quinazolin-6-yl]-2-[1-(2-methoxyethyl)piperidin-4-ylidene]acetamide disalicylate;

N-[4-(3-chloro-4-fluorophenylamino)-7-(2-methoxyethoxy)quinazolin-6-yl]-2-[1-(2-methoxyethyl)piperidin-4-ylidene]acetamide bis(4-aminosalicylate);

N-[4-(3-chloro-4-fluorophenylamino)-7-(2-methoxyethoxy)quinazolin-6-yl]-2-[1-(2-methoxyethyl)piperidin-4-ylidene]acetamide diacetyl salicylate;

N-[4-(3-chloro-4-fluorophenylamino)-7-(2-methoxyethoxy)quinazolin-6-yl]-2-[1-(2-methoxyethyl)piperidin-4-ylidene]acetamide ditartrate;

N-[4-(3-chloro-4-fluorophenylamino)-7-(2-methoxyethoxy)quinazolin-6-yl]-2-[1-(2-methoxyethyl)piperidin-4-ylidene]acetamide di(p-toluenesulfonate);

N-[4-(3-chloro-4-fluorophenylamino)-7-(2-methoxyethoxy)quinazolin-6-yl]-2-[1-(2-methoxyethyl)piperidin-4-ylidene]acetamide dicitrate;

N-[4-(3-chloro-4-fluorophenylamino)-7-(2-methoxyethoxy)quinazolin-6-yl]-2-[1-(2-methoxyethyl)piperidin-4-ylidene]acetamide dimalate;

N-[4-(3-chloro-4-fluorophenylamino)-7-(2-methoxyethoxy)quinazolin-6-yl]-2-[1-(2-methoxyethyl)piperidin-4-ylidene]acetamide bis(naphthalene-1,5-disulfonate);

N-[4-(3-chloro-4-fluorophenylamino)-7-(2-methoxyethoxy)quinazolin-6-yl]-2-[1-(2-methoxyethyl)piperidin-4-ylidene]acetamide bis(decanedioate); and N-[4-(3-chloro-4-fluorophenylamino)-7-(2-methoxyethoxy)quinazolin-6-yl]-2-[1-(2-methoxyethyl)piperidin-4-ylidene]acetamide bis(L-aspartate).

\* \* \* \* \*